(12) United States Patent
Itoi

(10) Patent No.: US 7,909,755 B2
(45) Date of Patent: Mar. 22, 2011

(54) ENDOSCOPE APPLICATOR AND ENDOSCOPE APPARATUS

(75) Inventor: Hiromu Itoi, Saitama (JP)

(73) Assignees: Fujifilm Corporation, Tokyo (JP); SRJ Corporation, Kawachi-gun, Tochigi (JP)

( * ) Notice: Subject to any disclaimer, the term of this patent is extended or adjusted under 35 U.S.C. 154(b) by 839 days.

(21) Appl. No.: 11/045,346

(22) Filed: Jan. 31, 2005

(65) Prior Publication Data

US 2005/0171400 A1 Aug. 4, 2005

(30) Foreign Application Priority Data

Jan. 30, 2004 (JP) ................................ 2004-023713
Jan. 30, 2004 (JP) ................................ 2004-023715
Feb. 25, 2004 (JP) ................................ 2004-049467
Nov. 5, 2004 (JP) ................................ 2004-322798

(51) Int. Cl.
*A61B 1/00* (2006.01)
*A61B 1/04* (2006.01)
*A61B 1/12* (2006.01)

(52) U.S. Cl. ......... 600/153; 600/114; 600/156; 600/158

(58) Field of Classification Search .......... 600/114–116, 600/156, 158, 153; 604/27, 36, 43, 506, 604/510, 80, 81, 86, 87, 93.01, 95.01–95.05, 604/102.01, 102.02, 102.03, 103, 158–160, 604/164.01, 164.11, 172, 173, 239, 264, 604/267, 268, 39, 101.03

See application file for complete search history.

(56) References Cited

U.S. PATENT DOCUMENTS

| | | | | |
|---|---|---|---|---|
| 5,271,735 A | * | 12/1993 | Greenfeld et al. | 604/266 |
| 5,313,934 A | * | 5/1994 | Wiita et al. | 600/109 |
| 5,415,157 A | * | 5/1995 | Welcome | 600/121 |
| 5,425,723 A | * | 6/1995 | Wang | 604/523 |
| 5,863,287 A | * | 1/1999 | Segawa | 600/121 |
| 5,941,815 A | * | 8/1999 | Chang | 600/114 |

(Continued)

FOREIGN PATENT DOCUMENTS

DE 29 15 271 10/1980

(Continued)

OTHER PUBLICATIONS

Michael, Albrecht, Guide for flexible endoscope with reinforcements, Jan. 14, 1999 English translation of publication number: DE19729499-Vorrichtung zum Erleichtern der Vorschubbewegung von flexiblen Endoskopen, Translation retrieved from EPO: Data supplied from the esp@cenet database-Worldwide.*

(Continued)

*Primary Examiner* — Linda C Dvorak
*Assistant Examiner* — Alireza Nia
(74) *Attorney, Agent, or Firm* — Young & Thompson

(57) ABSTRACT

The endoscope applicator according to the present invention allows lubricant to be supplied uniformly to the entire inner surface of the endoscope applicator without increasing the diameter of the endoscope applicator because the lubricant supply path is laid on the outer surface of the endoscope applicator extending from the base end portion to the tip portion of the endoscope applicator and a plurality of openings are formed in the lubricant supply path and endoscope applicator at predetermined intervals in such a way that their opening areas of the opening increase from the base end portion to the tip portion. Moreover, the endoscope apparatus according to the present invention can improve the maneuverability of the insert portion and applicator during pull-in operation. Furthermore, the endoscope apparatus according to the present invention makes it possible to determine pull-out force quantitatively.

15 Claims, 20 Drawing Sheets

U.S. PATENT DOCUMENTS

| | | | |
|---|---|---|---|
| 6,077,219 A * | 6/2000 | Viebach et al. | 600/114 |
| 6,086,530 A | 7/2000 | Mack | |
| 6,554,793 B1 | 4/2003 | Pauker et al. | |
| 7,150,713 B2 * | 12/2006 | Shener et al. | 600/156 |
| 7,223,263 B1 * | 5/2007 | Seno | 604/541 |
| 2003/0040737 A1 | 2/2003 | Merril et al. | |
| 2003/0069472 A1 | 4/2003 | Butler | |
| 2005/0043682 A1 * | 2/2005 | Kucklick et al. | 604/164.09 |

FOREIGN PATENT DOCUMENTS

| | | |
|---|---|---|
| DE | 197 29 499 | 1/1999 |
| DE | 101 11 354 | 9/2002 |
| JP | 10-248794 | 9/1998 |
| JP | 2001-340462 | 12/2001 |
| JP | 2002-301019 | 10/2002 |
| WO | WO 02/069841 | 9/2002 |
| WO | WO 2004/067053 | 8/2004 |

OTHER PUBLICATIONS

Brommersma, Pieter, Endoscope instrument shaft sliding medium supply comes in through sourced channel or grooved into shaft . . . , Sep. 19, 2002, English translation of publication number: DE10111354-Endoskopisches Instrument mit Gleitmittelbeaufschlagung, Translation retrieved from EPO: Data supplied from the esp@cenet database-Worldwide.*

C.A. Mosse et al. "Device for measuring the forces exerted on the shaft of an endoscope during colonscopy", Medical and Biological Engineering and computing, vol. 36, No. 2, Mar. 1998, pp. 186-190.

* cited by examiner

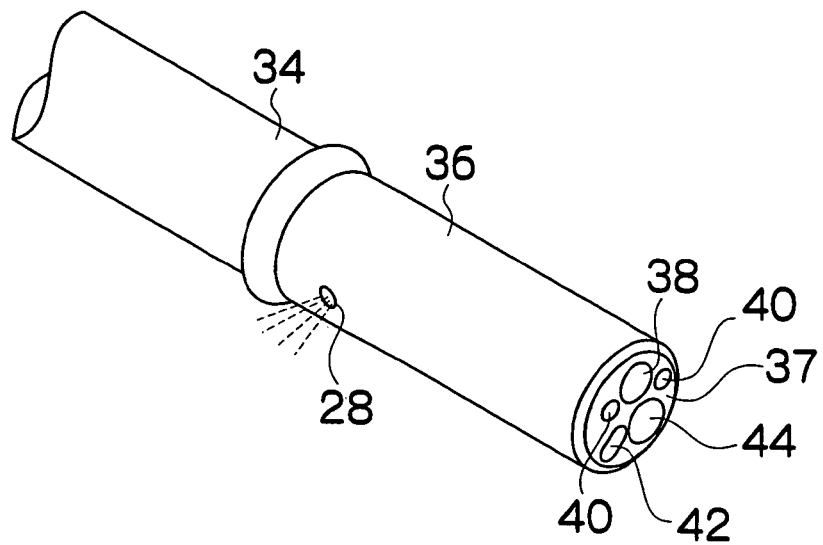
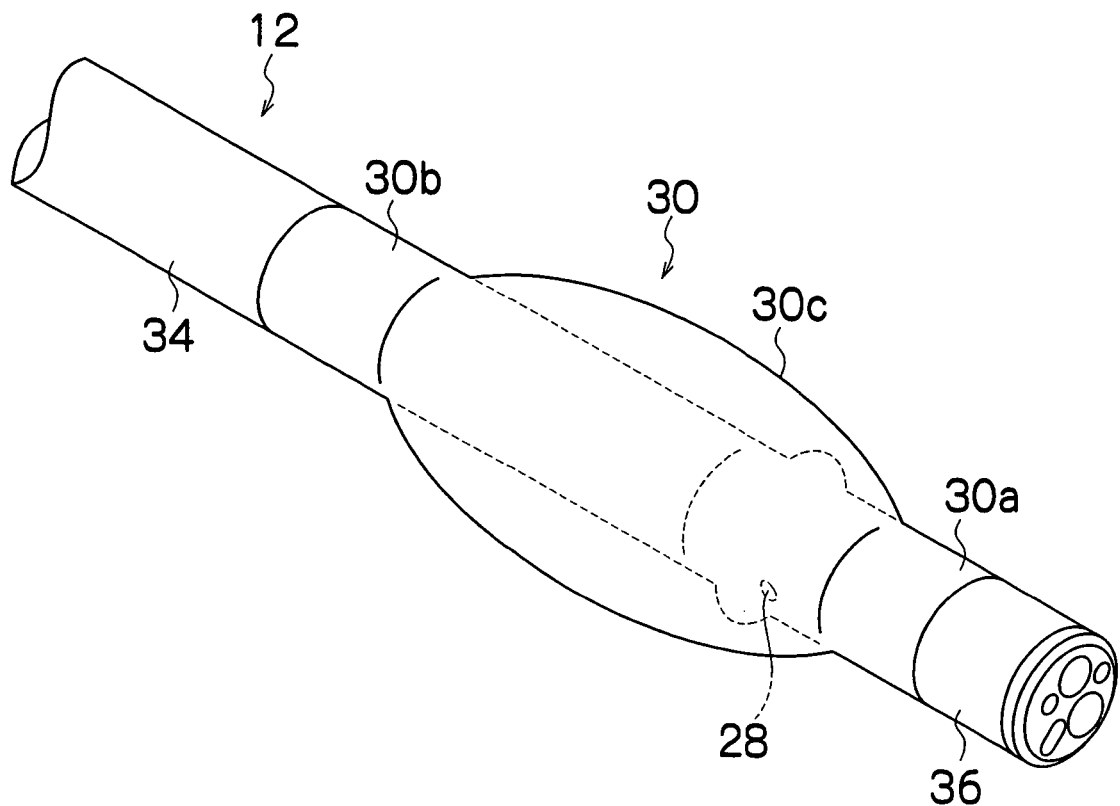
FIG. 3

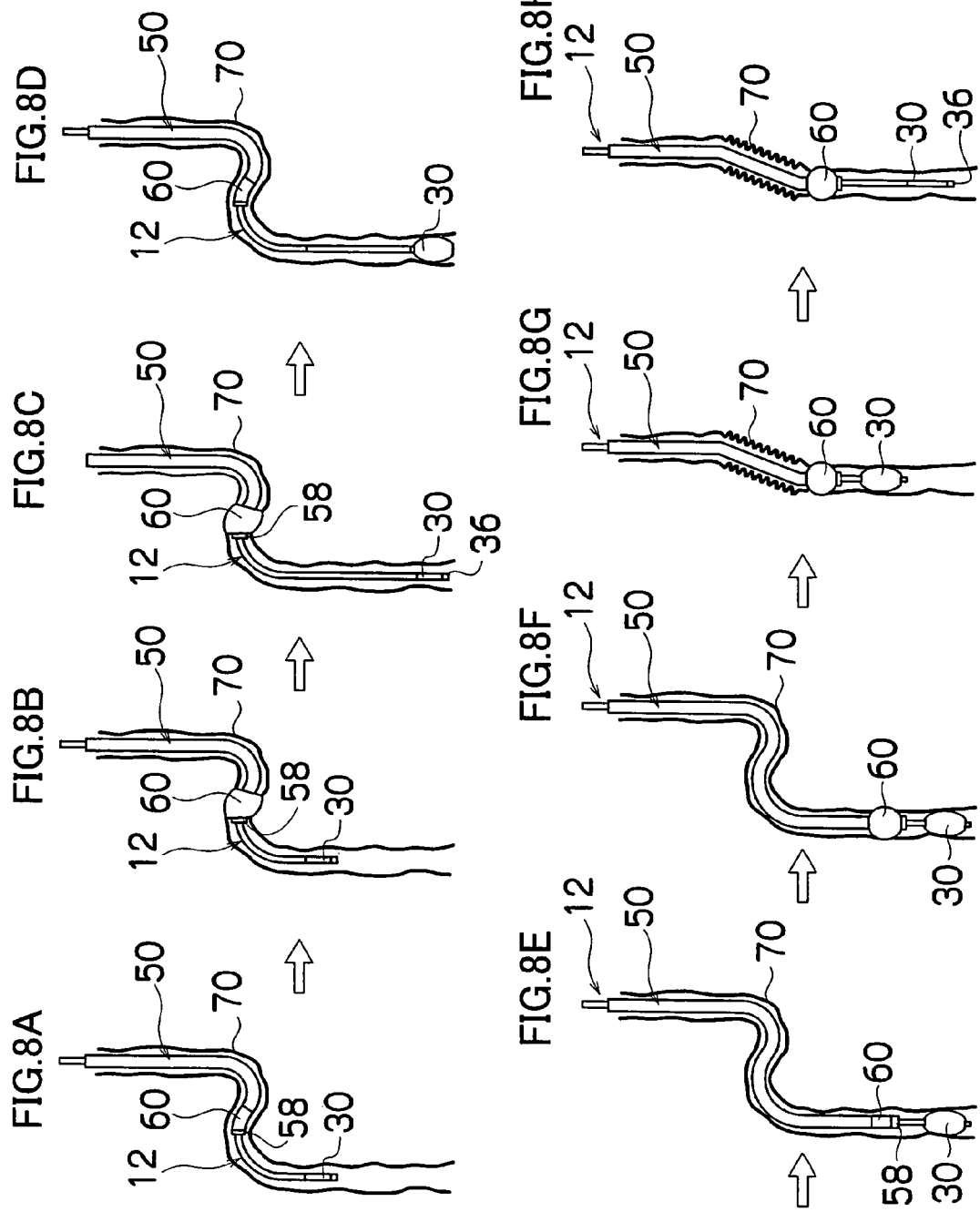

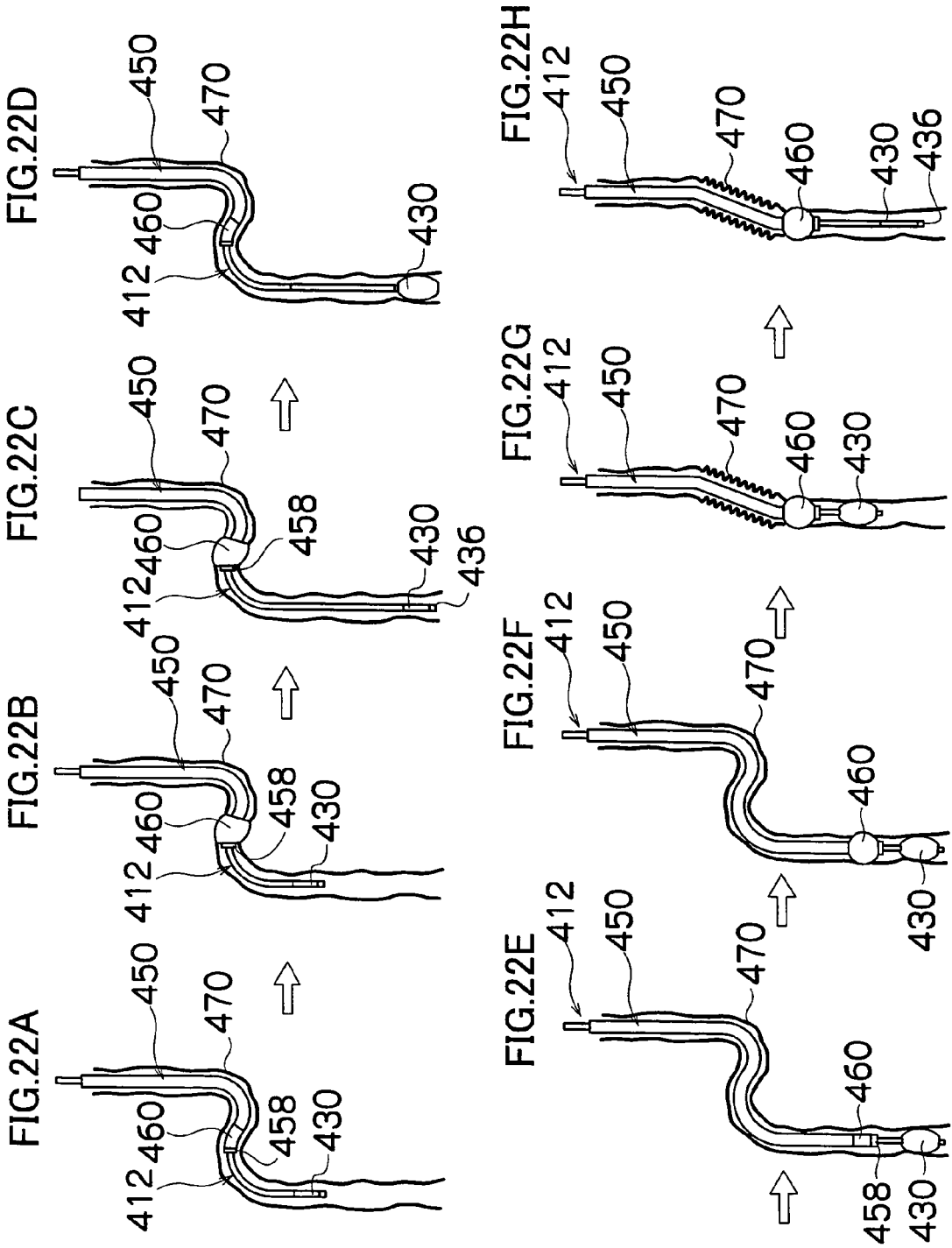

US 7,909,755 B2

ENDOSCOPE APPLICATOR AND ENDOSCOPE APPARATUS

BACKGROUND OF THE INVENTION

1. Field of the Invention

The present invention relates to an endoscope applicator and endoscope apparatus. More particularly, it relates to an endoscope applicator for use to insert an insert portion of an endoscope into a body cavity as well as to an endoscope apparatus which uses the applicator.

2. Description of the Related Art

When inserting an insert portion of an endoscope into a deep digestive tract such as a small intestine, it is difficult to insert the insert portion into the depth by simply pushing the insert portion because the force is not transmitted readily to the tip of the insert portion due to complicated bends in the intestinal tract. To deal with this situation, an endoscope apparatus has been proposed which inserts the insert portion of the endoscope into the body cavity by fitting an applicator called an overtube or sliding tube over the insert portion, guides the insert portion by the applicator, and thereby prevents excess bending and flexion of the insert portion (e.g., Japanese Patent Application Laid-open No. 10-248794). Incidentally the overtube is an applicator used in the small intestine while the sliding tube is an applicator used in the large intestine.

Also, it has been proposed to form a lubricant inlet at a base end portion of the conventional overtube, pour lubricant through the inlet into the base end portion of the overtube, and thereby improve slidability of the endoscope insert portion along the overtube, reducing the time required for endoscopic procedures. Water, a physiological salt solution, or the like is used as the lubricant.

Furthermore, known endoscope apparatus include double-balloon endoscope apparatus which have a first balloon at a tip portion of the endoscope insert portion and a second balloon at a tip of portion the applicator (e.g., Japanese Patent Application Laid-open Nos. 2001-340462 and 2002-301019).

With a double-balloon endoscope apparatus, the bent intestinal tract is sometimes contracted in a straightened state by inserting a predetermined length of the insert portion and applicator in the intestinal tract, inflating the two balloons, and pulling in the insert portion and applicator simultaneously with the two balloons placed in intimate contact with intestinal walls. Subsequently, the insert portion and applicator are pushed and pulled repeatedly to draw up the intestinal tract and put the insert portion in a desired site. In the pull-in operation, the physician grips the applicator made of an elastic member, thereby bringing it into intimate contact with the insert portion by elastic deformation, and pulls in the applicator, thereby pulling in the insert portion at the same time by means of frictional resistance between the applicator and insert portion (e.g., Japanese Patent Application Laid-open No. 10-248794).

When the inflated first balloon or second balloon comes into too intimate contact with, or adheres to, intestinal walls, if the physician pulls in (pull out) the insert portion and overtube forcibly, the intestinal walls may be damaged. In such a case, i.e., if the physician feels a strong pull-out resistance, conventionally he/she lowers the adhesive force by rotating the overtube or insert portion before resuming the pull-in operation.

SUMMARY OF THE INVENTION

However, there is a problem: in the case of the conventional overtube with a lubricant inlet formed at the base end portion, the lubricant poured through the inlet is not distributed sufficiently over the entire inner surface of the overtube, and thus it is not possible to further improve slidability of the endoscope insert portion.

This problem can be solved if the diameter of the overtube is enlarged, increasing the clearance between the overtube and endoscope insert portion and thereby allowing the lubricant supplied to the base end portion to be distributed over the entire inner surface of the overtube. However, since the overtube is inserted in the body cavity, preferably its diameter is minimized. This poses a dilemma: decreasing the diameter of the overtube makes it impossible to distribute the lubricant over the entire inner surface of the overtube while increasing the diameter of the overtube makes the overtube unsuitable as a member to be inserted in the body cavity.

The conventional double-balloon endoscope apparatus have the disadvantage of poor maneuverability because the insert portion tends to slip along the applicator during the pull-in operation.

Moreover, conventionally the physician determines his/her subsequent action (whether to continue pulling in the insert portion and overtube or rotate the insert portion and overtube) upon encountering a pull-out resistance. Consequently, there has been a demand for an endoscope apparatus which makes it possible to quantitatively determine the pull-out resistance produced when the insert portion and applicator are pulled in and perform subsequent operations properly.

The present invention has been made in view of the above circumstances and has an object to provide an endoscope applicator which allows lubricant to be supplied uniformly to the entire inner surface of the applicator without increasing the diameter of the applicator.

The present invention has been made in view of the above circumstances and has another object to provide an endoscope apparatus which can improve the maneuverability of an insert portion and applicator when they are pulled in.

The present invention has been made in view of the above circumstances and has another object to provide an endoscope apparatus which allows the pull-out resistance of an applicator or overtube, and an insert portion to be determined quantitatively.

To achieve the above objects, a first aspect of the present invention provides an endoscope applicator which allows an endoscope insert portion to be inserted through a base end portion of the endoscope applicator and allows lubricant to be poured through a lubricant inlet formed at the base end portion, wherein a lubricant supply path is formed in the endoscope applicator to allow the lubricant supplied to the lubricant inlet to be supplied to a clearance between an inner surface of the endoscope applicator and an outer surface of the endoscope insert portion.

The first aspect of the present invention has been made in view of the fact that between the endoscope insert portion and the endoscope applicator, the part which particularly needs enhanced lubricity is the tip portion of the endoscope applicator where the endoscope insert portion is rubbed by an inner edge of an opening portion at the tip of the applicator. As described in the first aspect, by forming a lubricant supply path in the endoscope applicator to allow the lubricant supplied to the lubricant inlet to be supplied to a clearance between an inner surface of the endoscope applicator and an outer surface of the endoscope insert portion, it is possible to supply the lubricant directly to the tip portion of the endoscope applicator. Thus, the present invention can improve the lubricity of the part which particularly needs enhanced lubricity.

A second aspect of the present invention provides the endoscope applicator according to the first aspect, wherein a plurality of openings are formed in the endoscope applicator at predetermined intervals to supply the lubricant poured into the lubricant supply path to the inside of the endoscope applicator. A third aspect of the present invention provides the endoscope applicator according to the second aspect, wherein opening areas of the plurality of openings increase from base end portion to tip portion of the endoscope applicator.

According to the second aspect of the present invention, the lubricant poured through the lubricant inlet flows to the lubricant supply path, and is subsequently supplied to the inside of the endoscope applicator via the plurality of openings formed in the applicator. Since the plurality of openings are formed from the base end portion to the tip portion of the endoscope applicator at predetermined intervals, the lubricant is supplied to the entire inner surface of the endoscope applicator. Furthermore, as described in the third aspect of the present invention, since the opening areas of the openings increase from the base end portion to the tip portion of the endoscope applicator, a uniform amount of lubricant is supplied over the entire inner surface of the endoscope applicator. Thus, the present invention allows lubricant to be supplied uniformly to the entire inner surface of the endoscope applicator without increasing the diameter of the endoscope applicator. This constantly provides good sliding characteristics, and thereby improves slidability of the insert portion along the endoscope applicator, reducing the time required for endoscopic procedures. Also, since good sliding characteristics are obtained constantly, it is possible to provide an endoscope applicator of a small diameter by decreasing the inside and outside diameters of the endoscope applicator and reducing the inside diameter of the endoscope applicator close to the diameter of the endoscope insert portion.

A fourth aspect of the present invention provides the endoscope applicator according to the third aspect, wherein a plurality of lubricant supply paths are provided. By providing a plurality of lubricant supply paths in the endoscope applicator, it is possible to form a plurality of openings on the circumference of the applicator, and thereby supply a more uniform amount of lubricant over the entire inner surface of the endoscope applicator.

A fifth aspect of the present invention provides the endoscope applicator according to the fourth aspect, wherein the lubricant supply path is installed spirally on the outer surface of the endoscope applicator. This makes it possible to form a plurality of openings on the circumference of the endoscope applicator using the single lubricant supply path, allowing lubricant to be supplied more uniformly to the entire inner surface of the endoscope applicator than when a single straight lubricant supply path is used.

To achieve the above objects, a sixth aspect of the present invention provides an endoscope apparatus, comprising: an endoscope with a balloon attached to a tip portion of an insert portion; and an applicator through which the insert portion of the endoscope is inserted into a body cavity, wherein an inner surface of the applicator is equipped with an engaging portion which engages with an outer surface of the insert portion when the applicator is squeezed and deformed.

According to the sixth aspect of the present invention, the inner surface of the applicator is equipped with an engaging member which engages with the outer surface of the insert portion to prevent relative slippage of the insert portion along the applicator when the applicator is squeezed and deformed elastically in such a direction as to reduce the diameter. Therefore, it is possible to prevent the insert portion from slipping along the applicator during pull-in operation. This improves the maneuverability of the insert portion and applicator when they are pulled in. The engaging member engages with the outer surface of the insert portion only when the applicator is deformed elastically, and the applicator is not deformed elastically when the insert portion is inserted and withdrawn into/from the applicator. Thus, the insertion/withdrawal operation is not affected adversely.

A seventh aspect of the present invention provides the endoscope apparatus according to the sixth aspect, wherein the outer surface of the insert portion is equipped with an engaged portion which is engaged with the engaging portion of the applicator. By forming the engaged member in the insert portion, it is possible to prevent slippage reliably and further improve maneuverability.

To achieve the above objects, an eighth aspect of the present invention provides an endoscope apparatus, comprising: an endoscope with a balloon attached to a tip portion of an insert portion; and an applicator through which the insert portion of the endoscope is inserted into a body cavity, wherein at least one of the insert portion and the applicator is equipped with a pull-out force measuring device which measures pull-out force of the insert portion or applicator. Since the insert portion or applicator is equipped with the pull-out force measuring device which measures the pull-out force of the insert portion or applicator, it is possible to determine the pull-out force quantitatively.

A ninth aspect of the present invention provides the endoscope apparatus according to the eighth aspect, further comprising a balloon pressure adjusting device which reduces internal pressure of the balloon when the pull-out force measured by the pull-out force measuring device exceeds a predetermined value. Since the internal pressure of the balloon is reduced by the balloon pressure adjusting device when the pull-out force measured by the pull-out force measuring device exceeds a predetermined value, it is possible to reduce frictional force between the balloon and intestinal walls, and thereby prevent damage to the intestinal walls. To adjust the internal pressure of the balloon by the balloon pressure adjusting device, it only needs to lower the internal pressure, and the easiest method in terms of control involves, for example, reducing the internal pressure by simply releasing air from the balloon.

A tenth aspect of the present invention provides an endoscope apparatus, comprising: an endoscope with a first balloon attached to a tip portion of an insert portion; and an overtube whose tip is equipped with a second balloon and through which the insert portion of the endoscope is inserted into a body cavity, wherein at least one of the insert portion and the overtube is equipped with a pull-out force measuring device which measures pull-out force of the insert portion or overtube. Since the insert portion or overtube is equipped with the pull-out force measuring device which measures the pull-out force of the insert portion or overtube, it is possible to determine the pull-out force quantitatively.

An eleventh aspect of the present invention provides the endoscope apparatus according to the tenth aspect, further comprising a balloon pressure adjusting device which reduces internal pressure of at least one of the first balloon and the second balloon when the pull-out force measured by the pull-out force measuring device exceeds a predetermined value. Since the internal pressure of the first balloon and/or second balloon is reduced by the balloon pressure adjusting device when the pull-out force measured by the pull-out force measuring device exceeds a predetermined value, it is possible to reduce frictional force between the balloons and intestinal walls, and thereby prevent damage to the intestinal walls. To adjust the internal pressure of the first balloon and/or second balloon by the balloon pressure adjusting device, it only needs to lower the internal pressure, and the easiest method in terms of control involves, for example, reducing the internal pressure by simply releasing air from the first balloon and/or second balloon.

According to a twelfth aspect of the present invention, the pull-out force measuring device is a strain gauge. Since the use of a strain gauge as the pull-out force measuring device makes it possible to detect minute strain in the insert portion, applicator, and overtube as an electrical signal and display it as electrical resistance, it is possible to determine the pull-out force quantitatively.

As described above, in the endoscope applicator according to the present invention, the lubricant supply path is laid on the outer surface of the applicator extending from the base end portion to the tip portion of the applicator and a plurality of openings are formed in the lubricant supply path and applicator at predetermined intervals in such a way that their opening areas of the opening increase from the base end portion to the tip portion. Therefore, the endoscope applicator allows lubricant to be supplied uniformly to the entire inner surface of the applicator without increasing the diameter of the applicator.

Moreover, in the endoscope apparatus according to the present invention, an engaging portion which engages with the outer surface of the insert portion is provided on the inner surface of the applicator when the applicator is squeezed and deformed. Therefore, it is possible to prevent the insert portion from slipping along the applicator during pull-in operation and thereby the maneuverability of the insert portion and applicator during pull-in operation is improved.

Furthermore, in the endoscope apparatus according to the present invention, the insert portion, applicator, and/or overtube are equipped with the pull-out force measuring device which measures the pull-out force of the insert portion, applicator, and/or overtube. Therefore, it is possible to determine pull-out force quantitatively.

BRIEF DESCRIPTION OF THE DRAWINGS

FIG. 2 is a perspective view showing a tip portion of an insert portion of an endoscope;

FIG. 3 is a perspective view showing a rigid tip portion of an insert portion equipped with a first balloon;

FIGS. 8A to 8H are explanatory diagrams illustrating how to operate the endoscope apparatus shown in FIG. 1;

FIGS. 22A to 22H are explanatory diagrams illustrating how to operate the endoscope apparatus shown in FIG. 17.

DETAILED DESCRIPTION OF THE PREFERRED EMBODIMENTS

Preferred embodiments of an endoscope applicator and endoscope apparatus according to the present invention will be described with reference to the accompanying drawings.

Figure 1:
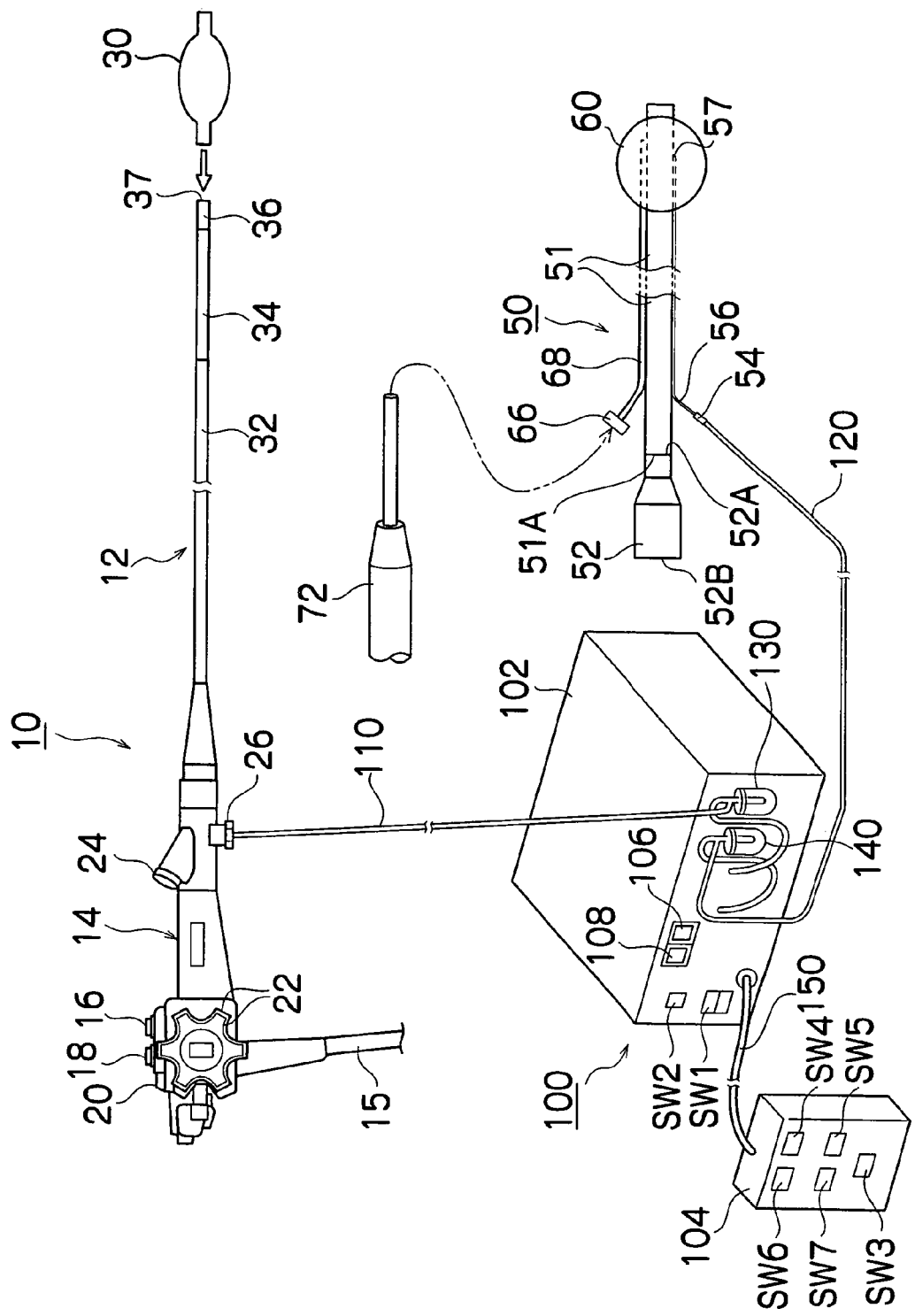
FIG. 1 is a system block diagram of an endoscope apparatus which employs an overtube according to the present invention.

FIG. 1 is a system block diagram of an endoscope apparatus which employs an endoscope applicator according to the present invention. The endoscope apparatus shown in the figure comprises an endoscope 10, overtube (applicator) 50, and balloon control apparatus 100.

The endoscope 10 is equipped with a hand controller 14 and an insert portion 12 provided in a row arrangement with the hand controller 14. The hand controller 14 is connected with a universal cable 15 whose tip is equipped with a connector (not shown) to be connected with a processor or light source (not shown).

The hand controller 14 is equipped with an air/water feed button 16, an aspiration button 18, and an shutter button 20, which are provided in proximity in a row arrangement and operated by the physician. Also, it is equipped with a pair of angle knobs 22 and a forceps inlet 24, which are placed at predetermined locations. Furthermore, the hand controller 14 is equipped with a balloon air feed port 26 to supply and suck air to/from a first balloon 30.

The insert portion 12 consists of a soft portion 32, a flexible portion 34, and a rigid tip portion 36. The flexible portion 34 is constructed from a plurality of joint rings connected flexibly. It is flexed remotely through rotation of the pair of angle knobs 22 mounted on the hand controller 14. This makes it possible to orient a tip surface 37 of a tip portion 36 in a desired direction.

As shown in FIG. 2, an objective optical system 38, an illumination lens 40, an air/water supply nozzle 42, a forceps port 44, etc. are mounted at predetermined locations on the tip surface 37 of the tip portion 36. Also, an air supply/suction port 28 opens to the outer surface of the tip portion 36. The air supply/suction port 28 is communicated with the balloon air feed port 26 in FIG. 1 via an air supply tube (not shown) which is approximately 0.8 mm in inside diameter and which is passed through the insert portion 12. Consequently, when air is fed to the balloon air feed port 26, the air supply/suction port 28 in the tip portion 36 emits air. When air is sucked through the balloon air feed port 26, the air supply/suction port 28 sucks air.

As shown in FIG. 1, the first balloon 30 made of an elastic body such as rubber is detachably attached to the tip portion 36 of the insert portion 12. As shown in FIG. 3, the first balloon 30 has an inflatable portion 30c in the center and mounting portions 30a and 30b on both ends. It is attached to the tip portion 36 in such a way that the air supply/suction port 28 is located on the inner side of the inflatable portion 30c. The mounting portions 30a and 30b have smaller diameters than the tip portion 36. They are brought into intimate contact with the tip portion 36 by their own elastic force and then fastened by a thread (not shown) wound around them. The fastening method is not limited to the use of a thread, and the mounting portions 30a and 30b may be fastened to the tip portion 36 by fitting retainer rings or rubber bands over the mounting portions 30a and 30b.

Of the first balloon 30 attached to the tip portion 36, the inflatable portion 30c is inflated into an approximately spherical shape by air supplied through the air supply/suction port 28 shown in FIG. 2. When air is sucked through the air supply/suction port 28, the inflatable portion 30c is deflated and brought into intimate contact with the outer surface of the tip portion 36.

Figure 4:
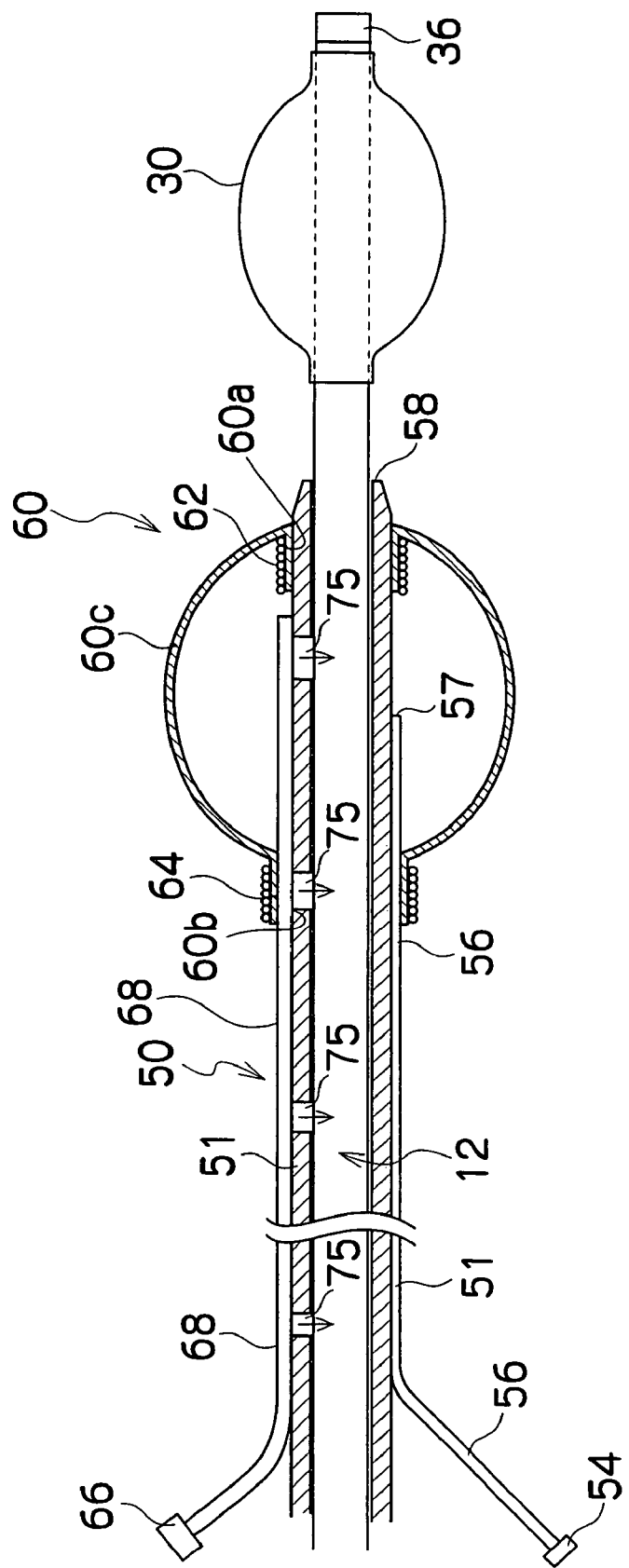
FIG. 4 is a sectional side view showing a tip portion of an overtube with an insert portion passed through it.

The overtube 50 shown in FIG. 1 has a tube body 51 and grip portion 52. As shown in FIG. 4, the tube body 51 is tubular in shape and has an inside diameter slightly larger than the outside diameter of the insert portion 12. Also, the tube body 51 is a molding of flexible urethane resin. Its inner and outer surfaces are covered with a lubricious coating. A connection port 52A formed at the tip of a rigid grip portion 52 is fitted watertight into a base end opening 51A of the tube body 51 to detachably connect the grip portion 52 to the tube body 51. Incidentally, the insert portion 12 is inserted into the tube body 51 through a base end opening 52B of the grip portion 52.

As shown in FIG. 1, a balloon air feed port 54 is provided at the base end of the tube body 51. The balloon air feed port 54 is connected with an air supply tube 56 approximately 1 mm in inside diameter. Being bonded to the outer surface of the tube body 51, the air supply tube 56 extends to the tip portion of the tube body 51 as shown in FIG. 1.

A tip 58 of the tube body 51 is tapered. A second balloon 60 made of an elastic body such as rubber is attached to the base end of the tip 58 of the tube body 51 in such a way as to be penetrated by the tube body 51. It has an inflatable portion 60c in the center and mounting portions 60a and 60b on both ends. The mounting portion 60a on the tip side is folded back into the inflatable portion 60c and fastened to the tube body 51, being wound by a radiopaque thread 62. The mounting portion 60b on the base end side is placed outside the second balloon 60 and fastened to the tube body 51, being wound by a thread 64.

The inflatable portion 60c has an approximately spherical shape in normal state (when neither inflated nor deflated) and is larger than the first balloon 30 in normal state (when neither inflated nor deflated). Thus, when air is fed to the first balloon 30 and the second balloon 60 at the same pressure, the inflatable portion 60c of the second balloon 60 becomes larger in outside diameter than the inflatable portion 30c of the first balloon 30. For example, when the outside diameter of the first balloon 30 is 25 mm, the outside diameter of the second balloon 60 is 50 mm.

The air supply tube 56 opens into the inflatable portion 60c by forming an air supply/suction port 57. Thus, when air is fed through the balloon air feed port 54, it blows out of the air supply/suction port 57 to inflate the inflatable portion 60c. On the other hand, when air is sucked out of the balloon air feed port 54, it is sucked through the air supply/suction port 57, deflating the second balloon 60.

The overtube 50 has a lubricant inlet 66, which is connected to a lubricant supply path 68. The lubricant supply path 68 is laid along the axis of the tube body 51, extending from the base end portion to the tip portion of the tube body 51 as shown in FIGS. 1 and 4. Also, a plurality of openings 75 are formed at predetermined intervals in the lubricant supply path 68 and the tube body 51 as shown in FIG. 4 to supply the lubricant poured into the lubricant supply path 68 to inside the tube body 51. The openings 75 are formed in such a way that their opening areas increase from the base end portion to the tip portion of the tube body 51. The intervals and opening areas of the openings 75 are determined according to the amount of lubricant supplied from a lubricant supply portion 72, such as a syringe shown in FIG. 1, connected to the inlet 66. That is, the intervals and opening areas which will allow lubricant to be supplied uniformly to the entire inner surface of the tube body 51 are determined based on the amount of lubricant supply. Alternatively, the amount of lubricant supply may be determined based on the intervals and opening areas of the openings 75.

Figure 5A:
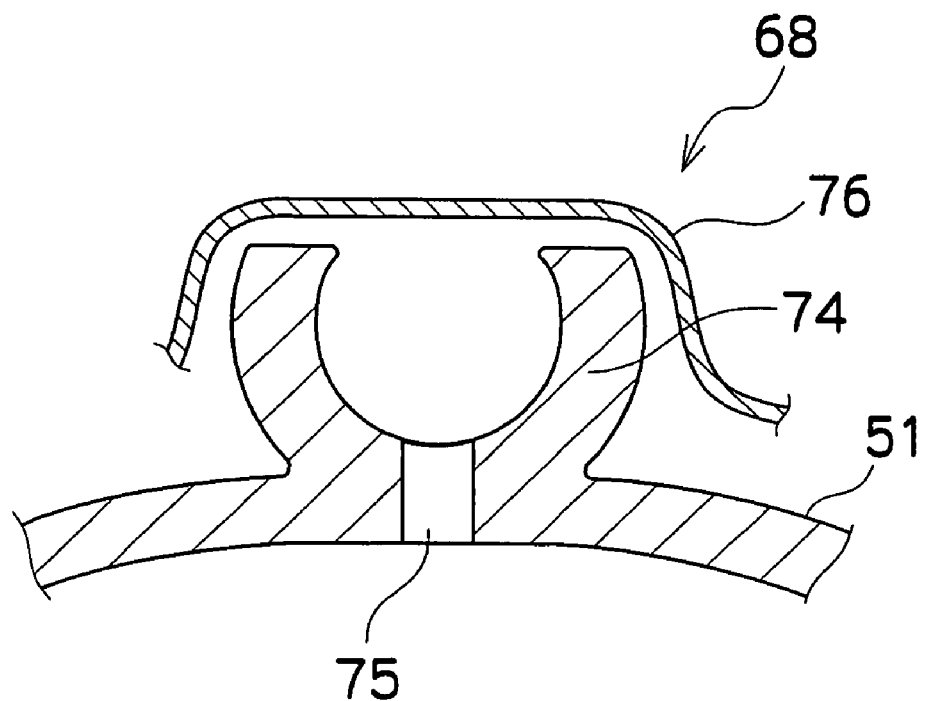
FIGS. 5A and 5B are enlarged sectional views of the essence part of a lubricant supply path formed in a tube body.
Figure 5B:
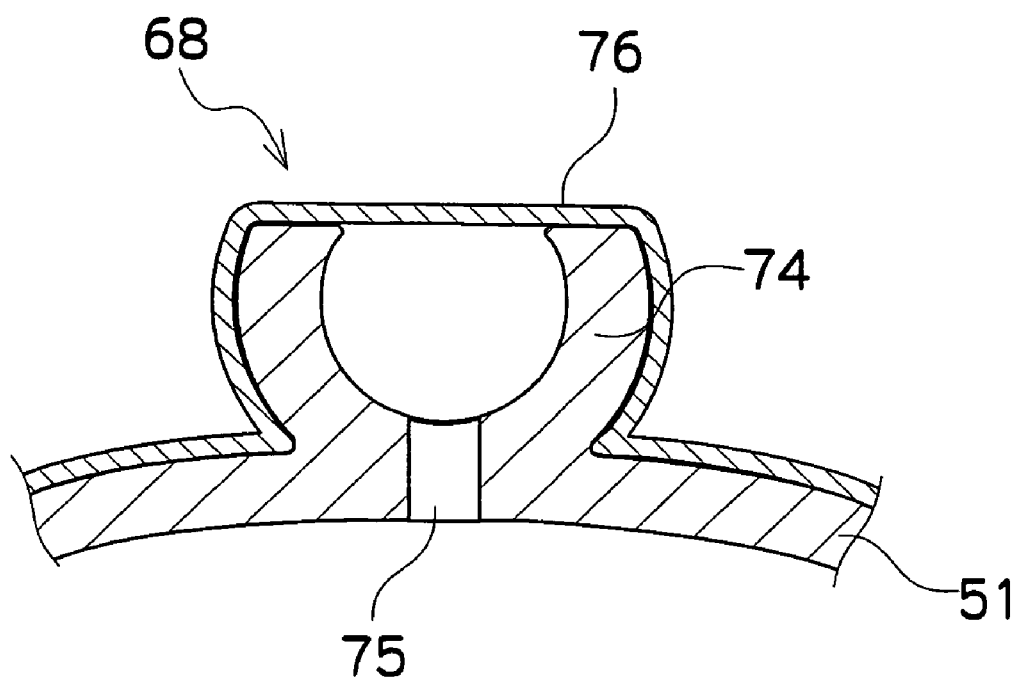

FIGS. 5A and 5B show an example of a manufacturing method of the lubricant supply path 68. FIGS. 5A and 5B are enlarged views of a portion near the lubricant supply path 68 with the tube body 51 cut along a plane orthogonal to the axial direction. As shown in FIG. 5A, a gutter member 74 with a U-shaped cross section is formed integrally with the tube body 51 and an opening 75 is formed in it by a subsequent process. A urethane-based heat-shrinkable sheet or tube 76 is put over the gutter member 74 or tube body 51 and is heat shrunk. This produces a lubricant supply path 68 made of the gutter member 74 and heat-shrinkable sheet or tube 76 as shown in FIG. 5B. Alternatively, the lubricant supply path 68 may be formed integrally with the tube body 51 in such a way as to be buried in the latter.

Figure 6:
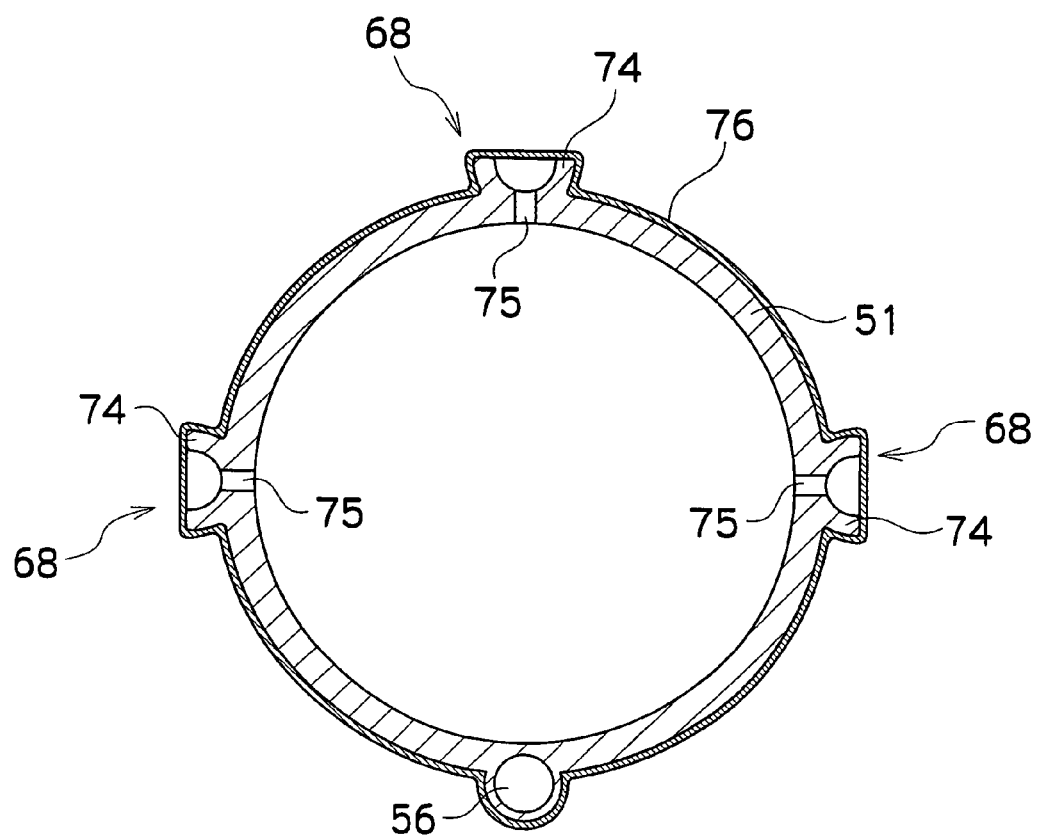
FIG. 6 is a sectional view of a tube body in which a plurality of lubricant supply paths are formed.
Figure 7A:
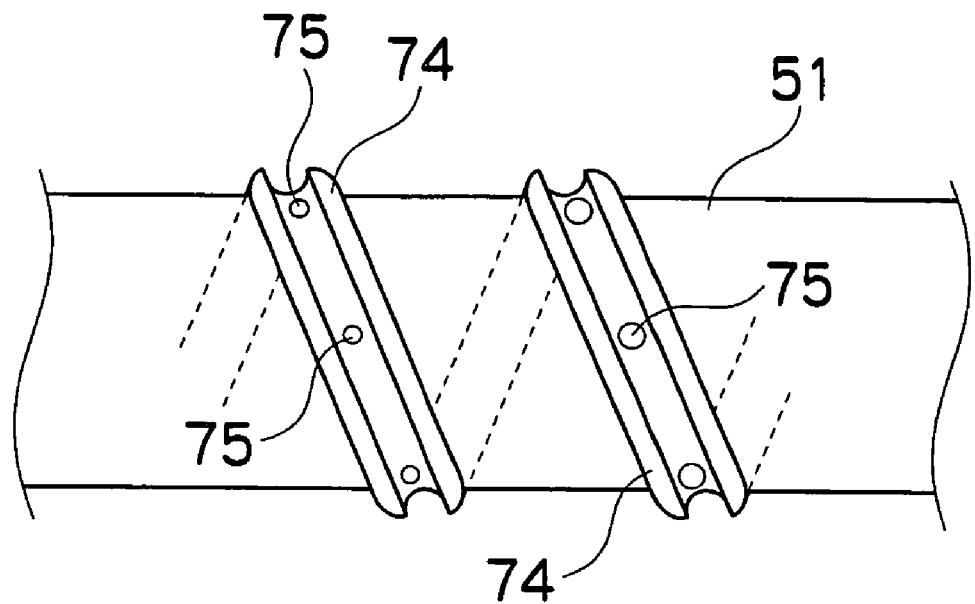
FIGS. 7A and 7B are explanatory diagrams illustrating an example in which a spiral lubricant supply path is formed on a tube body.
Figure 7B:
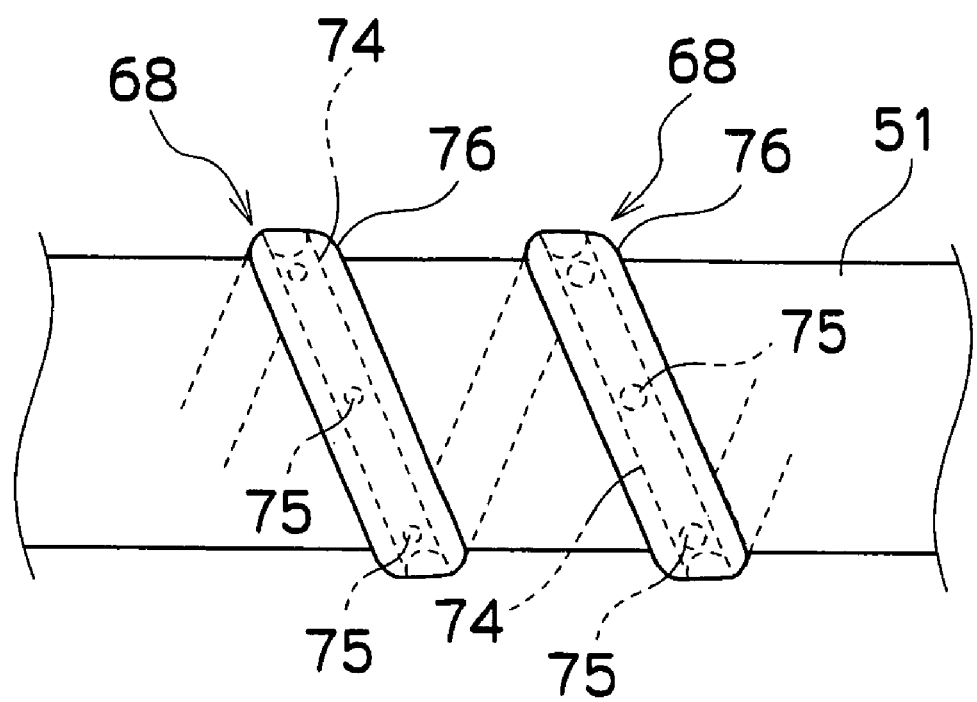

A plurality of lubricant supply paths 68 may be formed on the outer surface of the tube body 51 as shown in FIG. 6 (three lubricant supply paths in FIG. 6). It is possible to bond a separate gutter member 74 to the tube body 51 instead of forming the gutter member 74 integrally with the tube body 51, create openings 75, and heat-shrink a heat-shrinkable sheet or tube 76 to form a lubricant supply path 68 as shown in FIGS. 5A and 5B. Furthermore, it is possible to form or bond a gutter member 74 spirally around the tube body 51 as shown in FIG. 7A and heat-shrink a heat-shrinkable sheet or tube 76 to form a lubricant supply path 68 as shown in FIG. 7B. In FIGS. 7A and 7B again, the openings 75 are formed in such a way that their opening areas increase gradually from the base end portion to the tip portion of the tube body 51.

On the other hand, the balloon control apparatus 100 in FIG. 1 supplies and sucks a fluid such as air to/from the first balloon 30 as well as the second balloon 60. The balloon control apparatus 100 includes an apparatus body 102 equipped with a pump, sequencer, etc. (not shown) and a remote control hand switch 104.

A power switch SW1, a stop switch SW2, a pressure gauge 106 for the first balloon 30, and a pressure gauge 108 for the second balloon 60 are installed on a front panel of the apparatus body 102. Also, a tube 110 for use to supply and suck air to/from the first balloon 30 and a tube 120 for use to supply and suck air to/from the second balloon 60 are installed on the front panel of the apparatus body 102. The tubes 110 and 120 have liquid reservoir tanks 130 and 140, respectively, to collect liquid flowing backward from the first balloon 30 and second balloon 60 in case the first balloon 30 and the second balloon 60 burst, respectively.

The hand switch 104 contains a stop switch SW3 similar to the stop switch SW2 of the apparatus body 102, an ON/OFF switch SW4 for pressurization/depressurization of the first balloon 30, a pause switch SW5 for use to maintain the pressure of the first balloon 30, an ON/OFF switch SW6 for pressurization/depressurization of the second balloon 60, and pause switch SW7 for use to maintain the pressure of the second balloon 60. The hand switch 104 is electrically connected to the apparatus body 102 via a cable 150.

Being configured as described above, the balloon control apparatus 100 inflates the first balloon 30 and the second balloon 60 by supplying air to them and keeps the first balloon 30 and the second balloon 60 inflated by maintaining the air pressure at a fixed value. Also, it deflates the first balloon 30 and the second balloon 60 by sucking air from them and keeps the first balloon 30 and the second balloon 60 deflated by maintaining the air pressure at a fixed value.

Next, an operation method of the endoscope apparatus will be described with reference to FIGS. 8A to 8H.

First, as shown in FIG. 8A, the insert portion 12 is inserted in an intestinal tract (e.g., pars descendens duodeni) 70 with the overtube 50 put over the insert portion 12. At this time, the first balloon 30 and the second balloon 60 are kept deflated.

Next, as shown in FIG. 8B, with the tip 58 of the overtube 50 inserted to a bend of the intestinal tract 70, the second balloon 60 is inflated by air supplied to it. Consequently, the second balloon 60 is restrained by the intestinal tract 70 and the tip 58 of the overtube 50 is fixed to the intestinal tract 70.

Next, as shown in FIG. 8C, only the insert portion 12 of the endoscope 10 is inserted into the depth of the intestinal tract 70. Then, as shown in FIG. 8D, the first balloon 30 is inflated by air supplied to it. Consequently, the first balloon 30 is fixed to the intestinal tract 70. Since the first balloon 30 is smaller than the second balloon 60 when inflated, there is less strain on the intestinal tract 70. This prevents damage to the intestinal tract 70.

Next, after the second balloon 60 is deflated with air sucked from it, the overtube 50 is pushed in and inserted together with the insert portion 12 as shown in FIG. 8E. When the tip 58 of the overtube 50 is inserted to near the first balloon 30, the second balloon 60 is inflated with air supplied to it as shown in FIG. 8F. Consequently, the second balloon 60 is fixed to the intestinal tract 70. That is, the intestinal tract 70 is held by the second balloon 60.

Then, as shown in FIG. 8G, the overtube 50 is pulled in. This causes the intestinal tract 70 to contract in a straightened state, eliminating excess bending and flexion of the overtube 50. Incidentally, when the overtube 50 is pulled in, the first balloon 30 and the second balloon 60 are restrained by the intestinal tract 70, and the frictional resistance of the first balloon 30 is smaller than that of the second balloon 60. Thus, even if the first balloon 30 and the second balloon 60 move away from each other, since the first balloon 30 with the smaller frictional resistance slides over the intestinal tract 70, there is no fear that the intestinal tract 70 is damaged by being pulled by the first balloon 30 and the second balloon 60.

Next, as shown in FIG. 8H, the first balloon 30 is deflated with air sucked from it. Then, the tip portion 36 of the insert portion 12 is inserted as deeply as possible into the intestinal tract 70. That is, the insertion operation shown in FIG. 8C is performed again. This allows the tip portion 36 of the insert portion 12 to be inserted into the depth of the intestinal tract 70. To insert the insert portion 12 further, the fixing operation shown in FIG. 8D, the pushing operation shown in FIG. 8E, the holding operation shown in FIG. 8F, the pull-in operation shown in FIG. 8G, and the insertion operation shown in FIG. 8H can be repeated in this order. This allows the insert portion 12 to be inserted more deeply into the intestinal tract 70.

During endoscopic procedures, lubricant is supplied to the tube body 51 of the overtube 50 from the lubricant supply portion 72 in FIG. 1. The lubricant is poured through the inlet 66, flows to the lubricant supply path 68, and then is supplied to inside the tube body 51 via a plurality of openings 75 formed in the lubricant supply path 68 and tube body 51.

Since the plurality of openings 75 are formed at predetermined intervals from the base end portion to the tip portion of the tube body 51, lubricant is supplied to the entire inner surface of the tube body 51. Furthermore, since the opening areas of the openings 75 increase from the base end portion to the tip portion of the tube body 51, the lubricant is supplied uniformly to the entire inner surface of the tube body 51.

Thus, the overtube 50 according to this embodiment allows lubricant to be supplied uniformly to the entire inner surface of the tube body 51 without increasing the diameter of the tube body 51. This constantly provides good sliding characteristics, and thereby improves slidability of the insert portion 12 along the tube body 51, reducing the time required for endoscopic procedures. Also, since good sliding characteristics are obtained constantly, it is possible to provide a tube body 50 of a small diameter by decreasing the inside and outside diameters of the tube body 51 inserted into a body cavity and reducing the inside diameter of the tube body 51 close to the diameter of the endoscope insert portion 12.

Also, as shown in FIG. 6, by installing a plurality of lubricant supply paths 68 in the tube body 51, it is possible to form a plurality of openings 75 on the circumference of the tube body 51, and thereby supply a more uniform amount of lubricant over the entire inner surface of the tube body 51.

Furthermore, as shown in FIGS. 7A and 7B, by installing a lubricant supply path 68 spirally on the tube body 51, it is possible to form a plurality of openings 75 on the circumference of the tube body 51 using the single lubricant supply path 68, allowing lubricant to be supplied more uniformly to the entire inner surface of the tube body 51 than when a single straight lubricant supply path 68 is used.

Incidentally, although an overtube 50 with a balloon has been cited in this embodiment, the present invention is also applicable to a sliding tube which guides an endoscope insert portion into the body cavity without a balloon.

Figure 9:
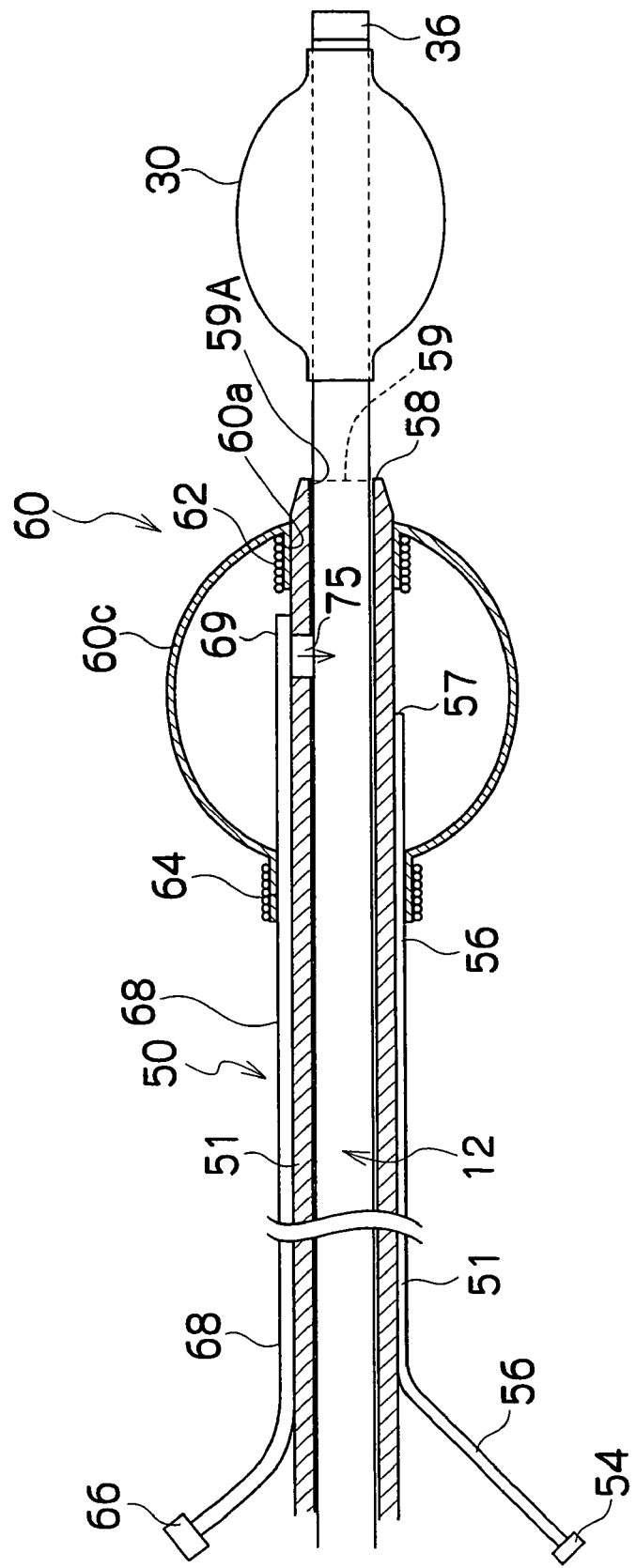
FIG. 9 is a sectional view of an overtube whose tip portion is supplied with a lubricant.

FIG. 9 is a sectional view of an embodiment of an overtube 50 where an opening 75 is formed only near the tip 58 of the tube body 51 of the overtube 50. The same or similar components as those of the overtube 50 shown in FIG. 4 are denoted by the same reference numerals as the corresponding components in FIG. 4 and description thereof will be omitted.

A lubricant supply path 68 communicated with an inlet 66 is laid on the outer surface of the tube body 51 in FIG. 9 extending from the base end portion to the tip 58 of the tube body 51 and an opening 75 which supplies the lubricant poured into the lubricant supply path 68 to the inside of the tube body 51 is formed near the tip 58 of the tube body 51 where the tip 69 of the lubricant supply path 68 is located.

Between the endoscope insert portion 12 and the tube body 51, the part which particularly needs enhanced lubricity is the tip 58 of the overtube 50 where the insert portion 12 is rubbed by an inner edge 59A of a tip opening 59 of the tube body 51. As is the case with the overtube 50 in FIG. 9, by forming the opening 75 near the tip 58 of the tube body 51 where the tip 69 of the lubricant supply path 68 is located, thereby allowing the lubricant poured into the lubricant supply path 68 to be supplied to the inside of the tube body 51, i.e., to the clearance between inner surface of the applicator and outer surface of the endoscope insert portion, it is possible to supply the lubricant directly to the tip 58 of the tube body 51. The overtube 50 in FIG. 9 can improve the lubricity of the tip 58 of the overtube 50 which particularly needs enhanced lubricity.

Figure 10:
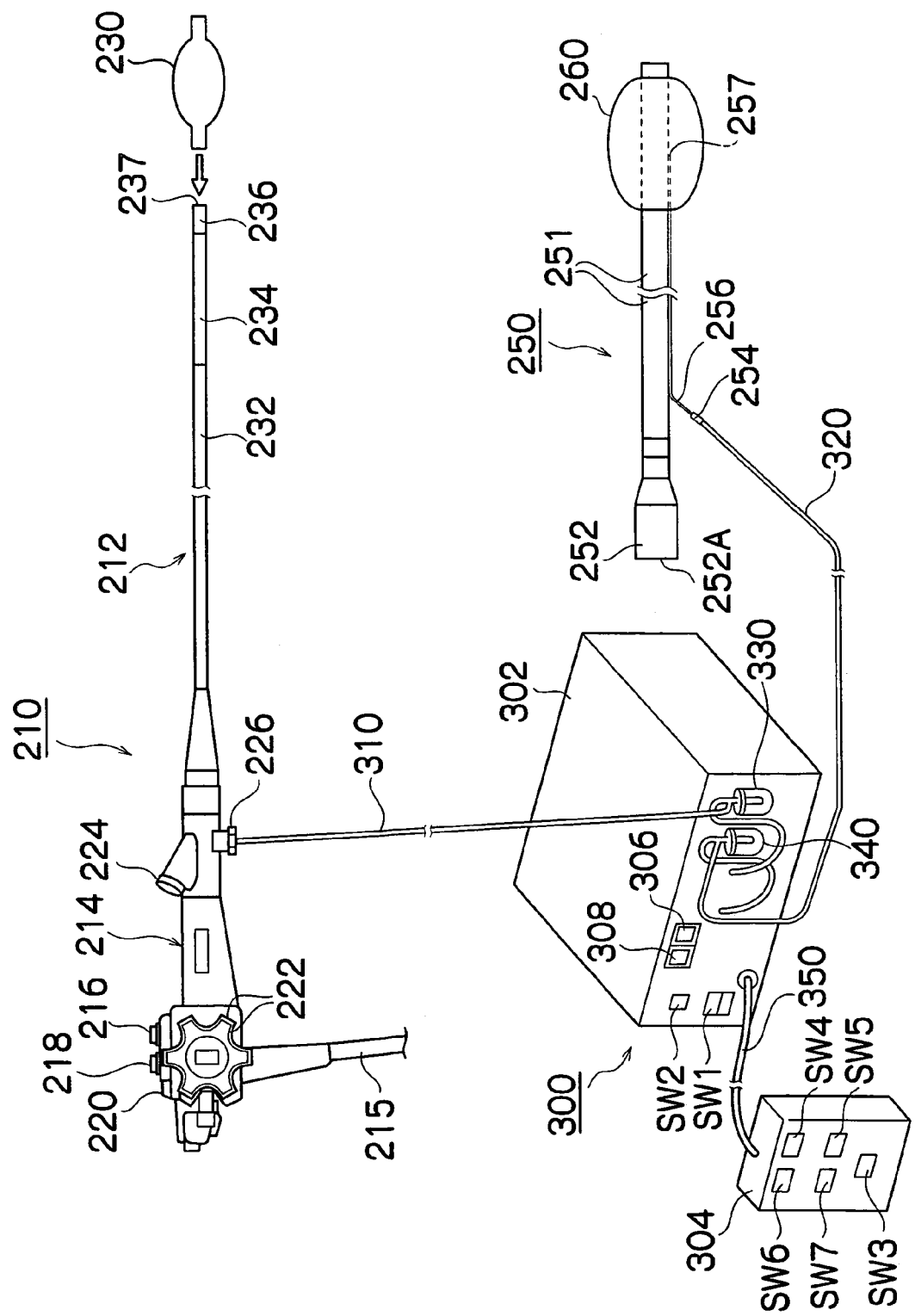
FIG. 10 is a system block diagram of an endoscope apparatus according to an embodiment the present invention.

FIG. 10 is a system block diagram of an endoscope apparatus according to an embodiment the present invention. The endoscope apparatus shown in the FIG. 10 comprises an endoscope 210, an overtube (corresponds to the applicator) 250, and a balloon control apparatus 300.

The endoscope 210 is equipped with a hand controller 214 and an insert portion 212 provided in a row arrangement with the hand controller 214. The hand controller 214 is connected with a universal cable 215 whose tip is equipped with a connector (not shown) to be connected with a processor or light source (not shown).

The hand controller 214 is equipped with an air/water feed button 216, aspiration button 218, and a shutter button 220, which are provided in proximity in a row arrangement and operated by the physician. Also, it is equipped with a pair of angle knobs 222 and a forceps inlet 224, which are placed at predetermined locations. Furthermore, the hand controller 214 is equipped with a balloon air feed port 226 to supply and suck air to/from a first balloon 230.

The insert portion 212 consists of a soft portion 232, a flexible portion 234, and a rigid tip portion 236. The flexible portion 234 is constructed from a plurality of joint rings connected flexibly. It is flexed remotely through rotation of the pair of angle knobs 222 mounted on the hand controller 214. This makes it possible to orient a tip surface 237 of a tip portion 236 in a desired direction.

Figure 11:
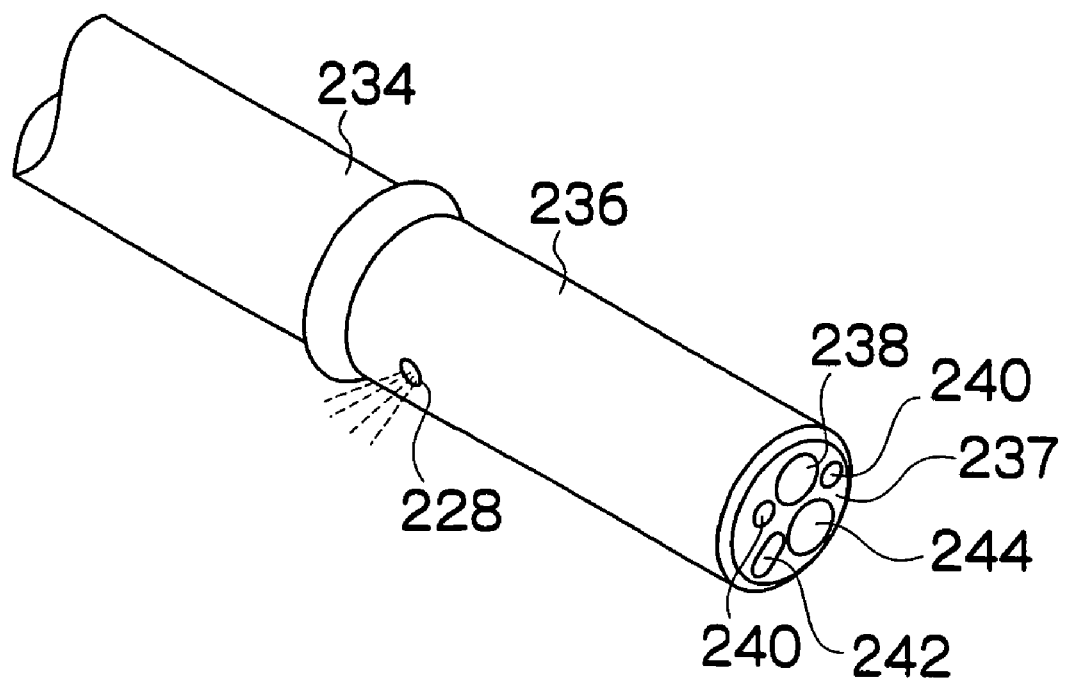
FIG. 11 is a perspective view showing a tip portion of an insert portion of an endoscope.

As shown in FIG. 11, an objective optical system 238, an illumination lens 240, an air/water supply nozzle 242, a forceps port 244, etc. are mounted at predetermined locations on the tip surface 237 of the tip portion 236. Also, an air supply/suction port 228 opens to the outer surface of the tip portion 236. The air supply/suction port 228 is communicated with the balloon air feed port 226 in FIG. 10 via an air supply tube (not shown) which is approximately 0.8 mm in inside diameter and which is passed through the insert portion 212. Consequently, when air is fed to the balloon air feed port 226, the air supply/suction port 228 in the tip portion 236 emits air. When air is sucked through the balloon air feed port 226, the air supply/suction port 228 sucks air.

Figure 12:
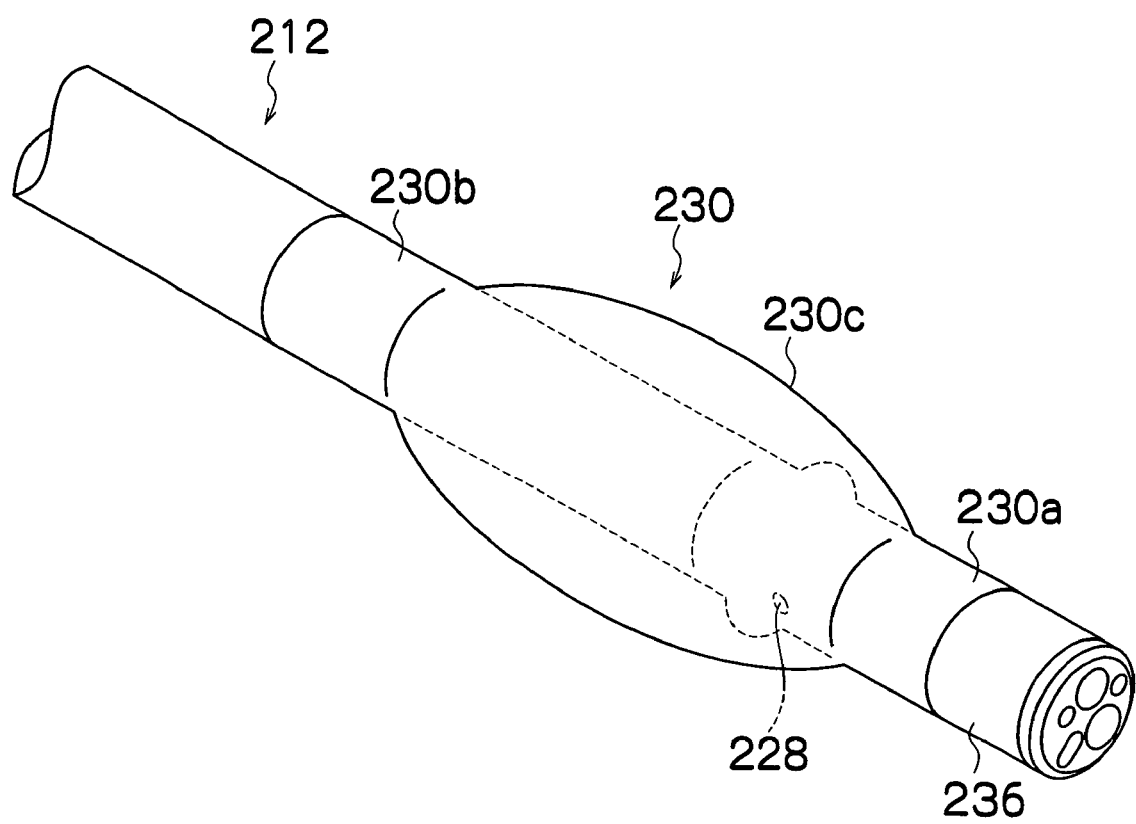
FIG. 12 is a perspective view showing a rigid tip portion of an insert portion equipped with a first balloon.

As shown in FIG. 10, the first balloon 230 made of an elastic body such as rubber is detachably attached to the tip portion 236 of the insert portion 212. As shown in FIG. 12, the first balloon 230 has an inflatable portion 230c in the center and mounting portions 230a and 230b on both ends. It is attached to the tip portion 236 in such a way that the air supply/suction port 228 is located on the inner side of the inflatable portion 230c. The mounting portions 230a and 230b have smaller diameters than the tip portion 236. They are brought into intimate contact with the tip portion 236 by their own elastic force and then fitted over the outer surface of the tip portion 236 securely with an annular band (not shown).

Of the first balloon 230 attached to the tip portion 236, the inflatable portion 230c is inflated into an approximately spherical shape by air supplied through the air supply/suction port 228 shown in FIG. 11. When air is sucked through the air supply/suction port 228, the inflatable portion 230c is deflated and brought into intimate contact with the outer surface of the tip portion 236.

Figure 13:
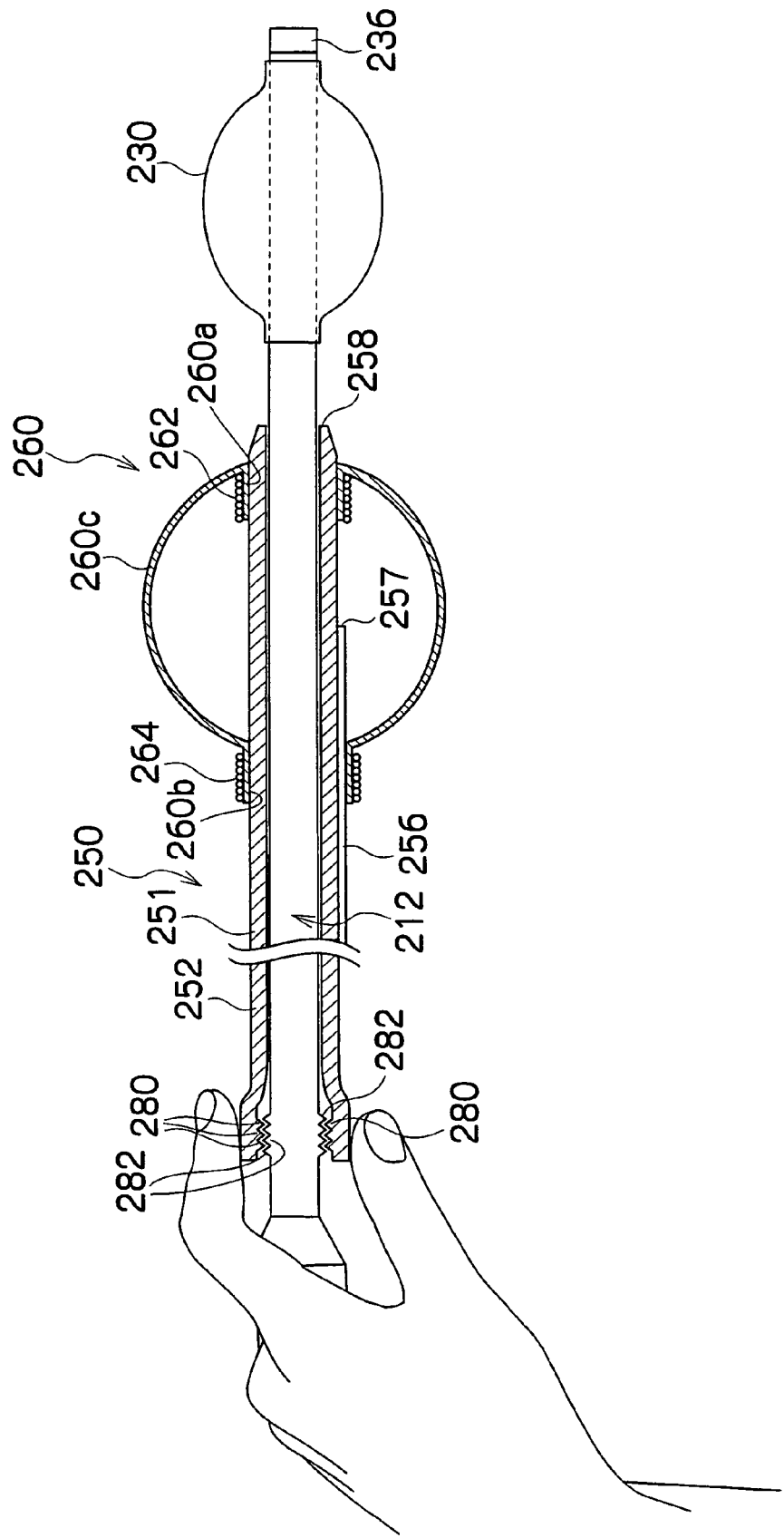
FIG. 13 is a sectional side view showing a tip portion of an overtube with an insert portion passed through it.

The overtube 250 shown in FIG. 10 has a tube body 251 and a grip portion 252. As shown in FIG. 13, the tube body 251 is tubular in shape and has an inside diameter slightly larger than the outside diameter of the insert portion 212. Also, the tube body 251 is a molding of flexible urethane resin. Its inner and outer surfaces are covered with a lubricious coating. The grip portion 252 is fitted watertight into the tube body 251 to detachably connect the grip portion 252 to the tube body 251. Incidentally, the insert portion 212 is inserted into the tube body 251 through a base end opening 252A of the grip portion 252.

As shown in FIG. 10, a balloon air feed port 254 is provided at the base end of the tube body 251. The balloon air feed port 254 is connected with an air supply tube 256 approximately 1 mm in inside diameter. Being bonded to the outer surface of the tube body 251, the air supply tube 256 extends to the tip portion of the tube body 251 as shown in FIG. 13.

A tip portion 258 of the tube body 251 is tapered to prevent intestinal walls from being caught in or the like. A second balloon 260 made of an elastic body such as rubber is attached to the base end of the tip portion 258 of the tube body 251 in such a way as to be penetrated by the tube body 251. It has an inflatable portion 260c in the center and mounting portions 260a and 260b on both ends. The mounting portion 260a on the tip side is folded back into the inflatable portion 260c and fastened to the tube body 251, being wound by a radiopaque thread 262. The mounting portion 260b on the base end side is placed outside the second balloon 260 and fastened to the tube body 251, being wound by a thread 264.

The inflatable portion 260c has an approximately spherical shape in normal state (when neither inflated nor deflated) and is larger than the first balloon 230 in normal state (when neither inflated nor deflated). Thus, when air is fed to the first balloon 230 and second balloon 260 at the same pressure, the inflatable portion 260c of the second balloon becomes larger in outside diameter than the inflatable portion 230c of the first balloon 230. For example, when the outside diameter of the first balloon 230 is 25 mm, the outside diameter of the second balloon 260 is 50 mm.

The air supply tube 256 opens into the inflatable portion 260c by forming an air supply/suction port 257. Thus, when air is fed through the balloon air feed port 254, it blows out of the air supply/suction port 257 to inflate the inflatable portion 260c. On the other hand, when air is sucked out of the balloon air feed port 254, it is sucked through the air supply/suction port 257, deflating the second balloon 260.

Figure 14:
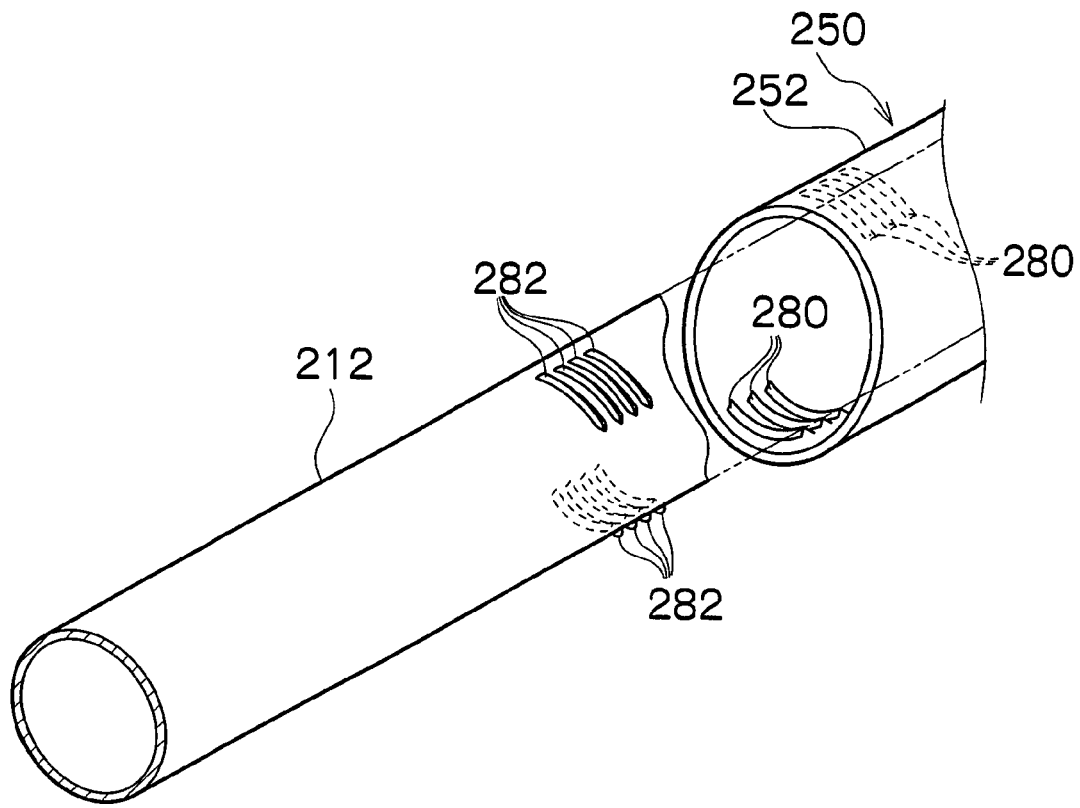
FIG. 14 is an explanatory diagram illustrating essential part, where antiskid members are formed on both overtube and insert portion.

An engaging portion 280 with multiple rows (three rows in FIG. 13) of serrations of a triangular cross section is formed as an antiskid member on the inner surface of the grip portion 252 of the overtube 250. As shown in FIG. 14, the engaging portion 280 is formed with a predetermined length in a direction orthogonal to the axial direction of the grip portion 252 and an engaging portion 280 with multiple rows (three rows in FIG. 14) of serrations is similarly formed on the opposite face.

Besides, an engaged portion 282 with multiple rows (four rows in FIG. 14) of serrations of a triangular cross section is formed as an antiskid member at a predetermined location on the outer surface of the insert portion 212. The engaged portion 282 is formed with a predetermined length in a direction orthogonal to the axial direction of the insert portion 212 and an engaged portion 282 with multiple rows (four rows in FIG. 14) of serrations is similarly formed on the opposite face.

Figure 15:
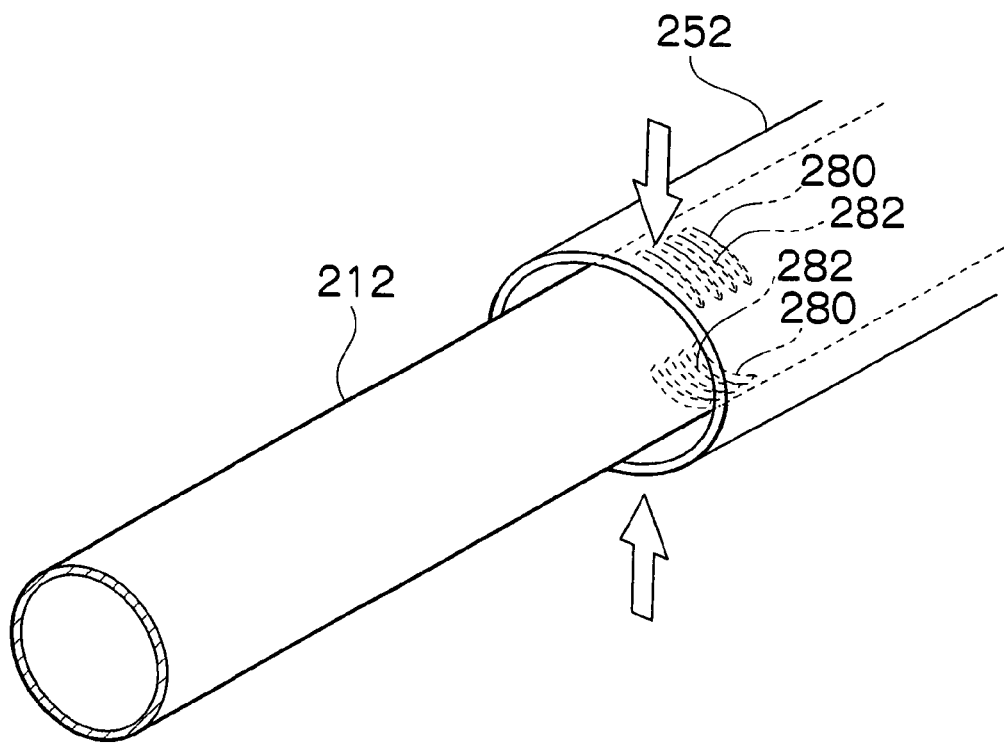
FIG. 15 is an explanatory diagram illustrating essential part, where antiskid members are engaged with each other.

The engaged portions 282 are not engaged with the engaging portions 280 of the grip portion 252 when the grip portion 252 is in normal state (when neither inflated nor deflated) as shown in FIG. 14. They are engaged, by being meshed, with the engaging portions 280 of the grip portion 252 as shown in FIG. 13 when the grip portion 252 is squeezed in the direction indicated by arrows and deformed elastically in a diameter-reducing direction as shown in FIG. 15. That is, the diameter of the grip portion 252 and heights of the engaging and engaged portions 280 and 282 are designed such that the grip portion 252 does not engage the engaging portions 280 and engaged portions 282 with each other in the normal state shown in FIG. 14. Also, the grip portion 252 is made of a soft material so as to engage the engaged portions 282 with the engaging portions 280 when deformed elastically.

Incidentally, the engaged portions 282 may be provided either continuously along the length of the insert portion 212 or in groups of rows formed at predetermined intervals. From the viewpoint of preventing the tip portion 258 from damaging the balloon 230, preferably the engaged portions 282 at the extreme tip of the insert portion 212 are formed in such a way that the balloon 230 will not touch the tip portion 258 of the overtube 250 as shown in FIG. 13 when the engaged portions 282 are engaged with the engaging portions 280.

On the other hand, the balloon control apparatus 300 in FIG. 10 supplies and sucks a fluid such as air to/from the first balloon 230 as well as the second balloon 260. The balloon control apparatus 300 includes an apparatus body 302 equipped with a pump, sequencer, etc. (not shown) and a remote control hand switch 304.

A power switch SW1, a stop switch SW2, a pressure gauge 306 for the first balloon 230, and a pressure gauge 308 for the second balloon 260 are installed on a front panel of the apparatus body 302. Also, a tube 310 for use to supply and suck air to/from the first balloon 230 and a tube 320 for use to supply and suck air to/from the second balloon 260 are installed on the front panel of the apparatus body 302. The tubes 310 and 320 have liquid reservoir tanks 330 and 340, respectively, to collect liquid flowing backward from the first balloon 230 and second balloon 260 in case the first balloon 230 and second balloon 260 burst, respectively.

The hand switch 304 contains a stop switch SW3 similar to the stop switch SW2 of the apparatus body 302, an ON/OFF switch SW4 for pressurization/depressurization of the first balloon 230, a pause switch SW5 for use to maintain the pressure of the first balloon 230, an ON/OFF switch SW6 for pressurization/depressurization of the second balloon 260, and a pause switch SW7 for use to maintain the pressure of the second balloon 260. The hand switch 304 is electrically connected to the apparatus body 302 via a cable 350.

Being configured as described above, the balloon control apparatus 300 inflates the first balloon 230 and second balloon 260 by supplying air to them and keeps the first balloon 230 and second balloon 260 inflated by maintaining the air pressure at a fixed value. Also, the balloon control apparatus 300 deflates the first balloon 230 and second balloon 260 by sucking air from them and keeps the first balloon 230 and second balloon 260 deflated by maintaining the air pressure at a fixed value.

Next, an operation method of the endoscope apparatus will be described with reference to FIGS. 16A to 16H.

Figure 16:
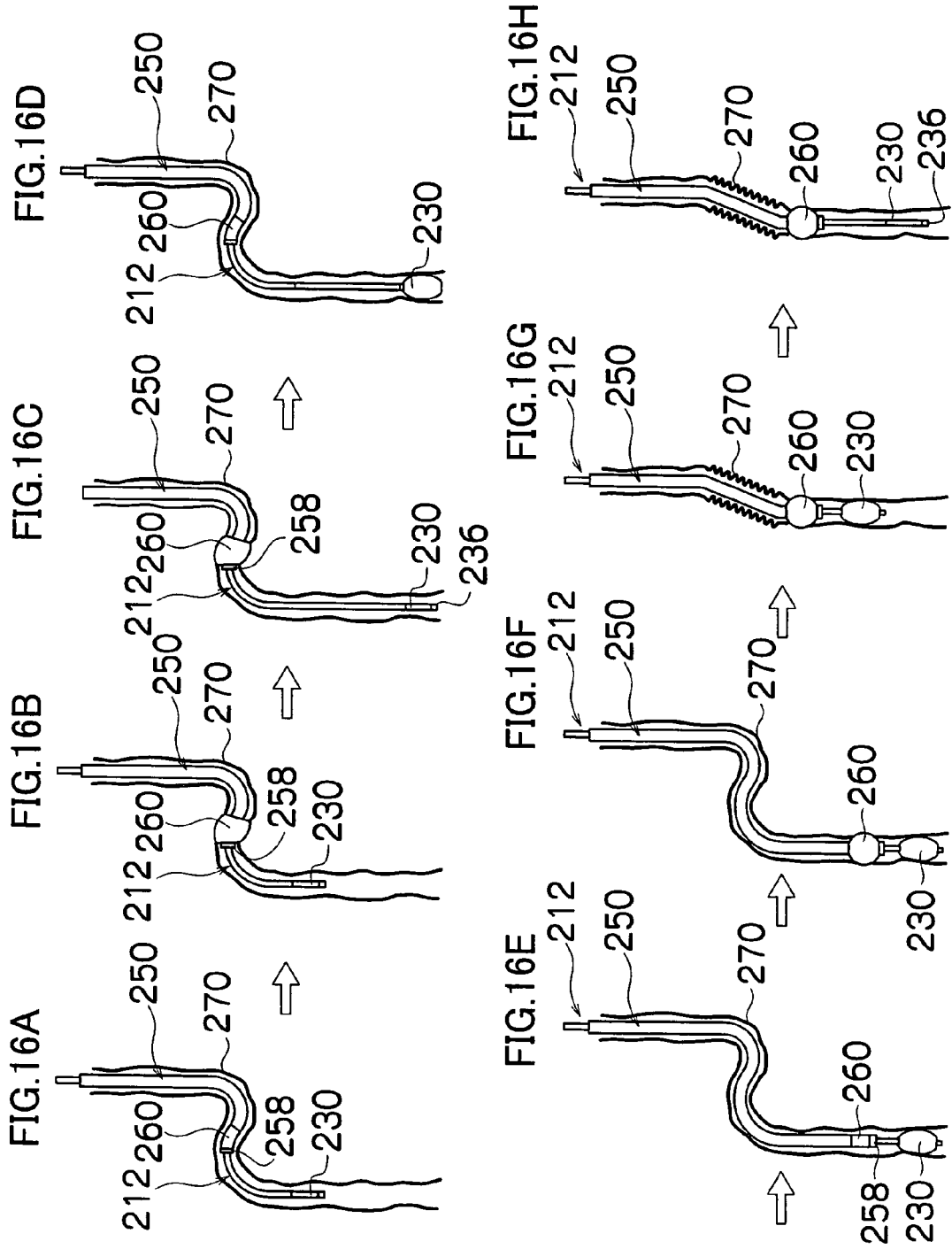
FIGS. 16A to 16H are explanatory diagrams illustrating how to operate the endoscope apparatus shown in FIG. 10.

First, as shown in FIG. 16A, the insert portion 212 is inserted in an intestinal tract (e.g., pars descendens duodeni) 270 with the overtube 250 put over the insert portion 212. At this time, the first balloon 230 and second balloon 260 are kept deflated.

Next, as shown in FIG. 16B, with the tip 258 of the overtube 250 inserted to a bend of the intestinal tract 270, the second balloon 260 is inflated by air supplied to it. Consequently, the second balloon 260 is restrained by the intestinal tract 270 and the tip 258 of the overtube 250 is fixed to the intestinal tract 270.

Next, as shown in FIG. 16C, only the insert portion 212 of the endoscope 210 is inserted into the depth of the intestinal tract 270. Then, as shown in FIG. 16D, the first balloon 230 is inflated by air supplied to it. Consequently, the first balloon 230 is fixed to the intestinal tract 270. Since the first balloon 230 is smaller than the second balloon 260 when inflated, there is less strain on the intestinal tract 270. This prevents damage to the intestinal tract 270.

Next, after the second balloon 260 is deflated with air sucked from it, the overtube 250 is pushed in and inserted together with the insert portion 212 as shown in FIG. 16E. When the tip 258 of the overtube 250 is inserted to near the first balloon 230, the second balloon 260 is inflated with air supplied to it as shown in FIG. 16F. Consequently, the second balloon 260 is fixed to the intestinal tract 270. That is, the intestinal tract 270 is held by the second balloon 260.

Then, as shown in FIG. 16G, the overtube 250 is pulled in. This causes the intestinal tract 270 to contract in a straightened state, eliminating excess bending and flexion of the overtube 250.

This operation involves pulling in the overtube 250 and insert portion 212 simultaneously. Before performing this operation, the physician grips the grip portion 252 as shown in FIG. 13, squeezes the grip portion 252 in the direction indicated by arrows in FIG. 15, and thereby deforms it elastically in a diameter-reducing direction to engage the engaged portions 282 of the insert portion 212 with the engaging portions 280 of the grip portion 252. In this state, the physician pulls in the overtube 250. Consequently, the insert portion 212 is pulled in together with the overtube 250 via the engaging and engaged portions 280 and 282, which are antiskid members, without slipping along the overtube 250.

When the overtube 250 is pulled in, the first balloon 230 and second balloon 260 are restrained by the intestinal tract 270, and the frictional resistance of the first balloon 230 is smaller than that of the second balloon 260. Therefore, even if the first balloon 230 and second balloon 260 move away from each other, the first balloon 230 with the smaller frictional resistance slides over the intestinal tract 270. Thus, there is no fear that the intestinal tract 270 is damaged by being pulled by the first balloon 230 and second balloon 260.

Next, as shown in FIG. 16H, the first balloon 230 is deflated with air sucked from it. Then, the tip portion 236 of the insert portion 212 is inserted as deeply as possible into the intestinal tract 270. That is, the insertion operation shown in FIG. 16C is performed again. This allows the tip portion 236 of the insert portion 212 to be inserted into the depth of the intestinal tract 270. To insert the insert portion 212 further, the fixing operation shown in FIG. 16D, the pushing operation shown in FIG. 16E, the holding operation shown in FIG. 16F, the pull-in operation shown in FIG. 16G, and the insertion operation shown in FIG. 16H can be repeated in this order. This allows the insert portion 212 to be inserted more deeply into the intestinal tract 270.

Incidentally, although according to this embodiment, antiskid members—the engaging portions 280 or engaged portions 282—are formed on both the overtube 250 and insert portion 212, antiskid members may be formed on only one of them if they provide the frictional resistance required during pull-in operation.

Also, although in this embodiment, the overtube 250 with the balloon 260 at the tip has been cited as an applicator, this is not restrictive and the antiskid members according to this embodiment may be provided on a sliding tube (an applicator without a balloon) used for a colonoscope.

Figure 17:
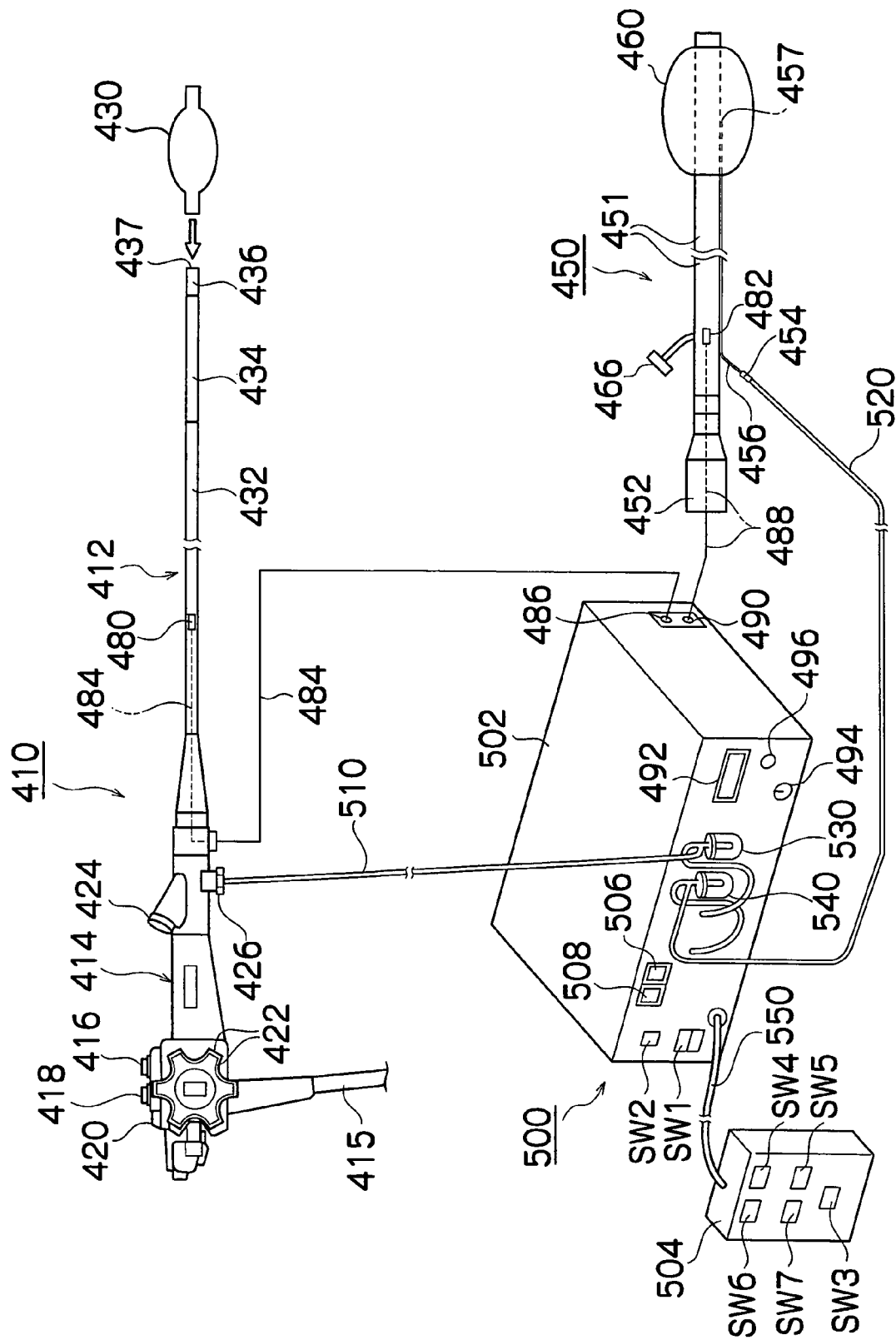
FIG. 17 is a system block diagram of an endoscope apparatus according to an embodiment the present invention.

FIG. 17 shows a block diagram of an endoscope apparatus according to an embodiment of the present invention. The endoscope apparatus shown in the FIG. 17 comprises an endoscope 410, an overtube 450, and a control apparatus 500.

The endoscope 410 is equipped with a hand controller 414 and an insert portion 412 provided in a row arrangement with the hand controller 414. The hand controller 414 is connected with a universal cable 415 whose tip is equipped with a connector (not shown) to be connected with a processor or light source (not shown).

The hand controller 414 is equipped with an air/water feed button 416, an aspiration button 418, and a shutter button 420, which are provided in proximity in a row arrangement and operated by the physician. Also, the hand controller 414 is equipped with a pair of angle knobs 422, 422 and a forceps inlet 424, which are placed at predetermined locations. Furthermore, the hand controller 414 is equipped with a balloon air feed port 426 to supply and suck air to/from a first balloon 430.

The insert portion 412 consists of a soft portion 432, a flexible portion 434, and a rigid tip portion 436. The flexible portion 434 is constructed from a plurality of joint rings connected flexibly. It is flexed remotely through rotation of the pair of angle knobs 422 mounted on the hand controller 414. This makes it possible to orient a tip surface 437 of a rigid tip portion 436 in a desired direction.

Figure 18:
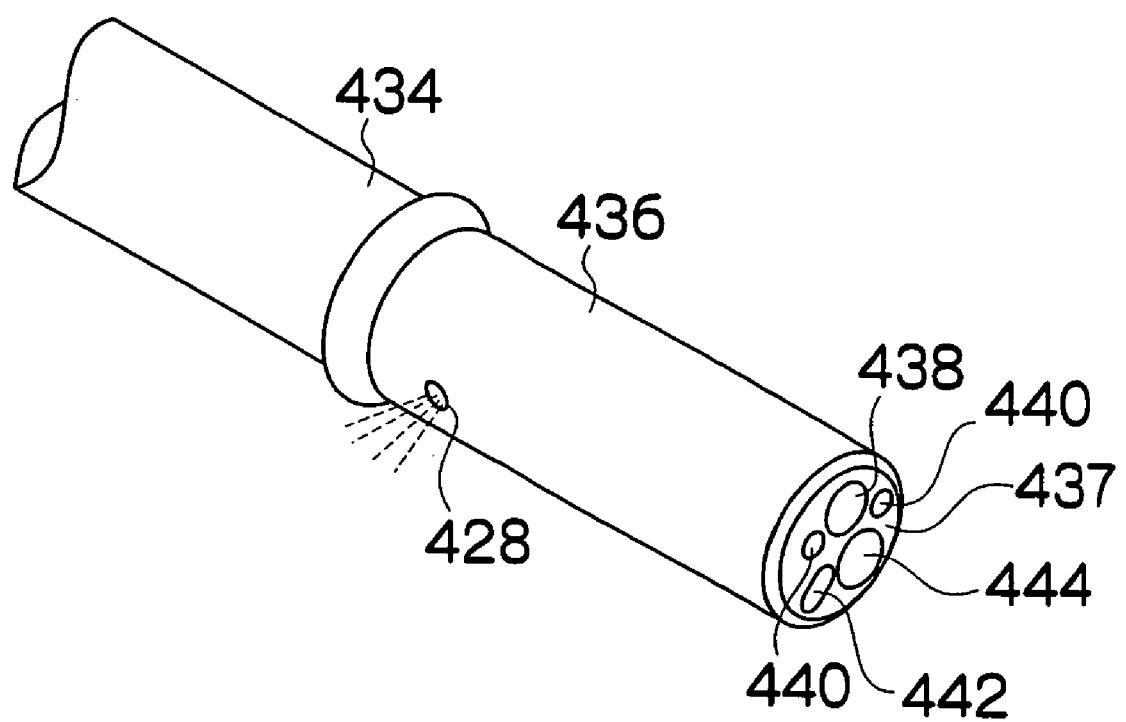
FIG. 18 is a perspective view showing a tip portion of an insert portion of an endoscope.

As shown in FIG. 18, an objective optical system 438, an illumination lens 440, an air/water supply nozzle 442, a forceps port 444, etc. are mounted at predetermined locations on the tip surface 437 of the rigid tip portion 436. Also, an air supply/suction port 428 opens to the outer surface of the rigid tip portion 436. The air supply/suction port 428 is communicated with the balloon air feed port 426 in FIG. 17 via an air supply tube (not shown) which is approximately 0.8 mm in inside diameter and which is passed through the insert portion 412. Consequently, when air is fed to the balloon air feed port 426, the air supply/suction port 428 in the rigid tip portion 436 emits air. When air is sucked through the balloon air feed port 426, the air supply/suction port 428 sucks air.

Figure 19:
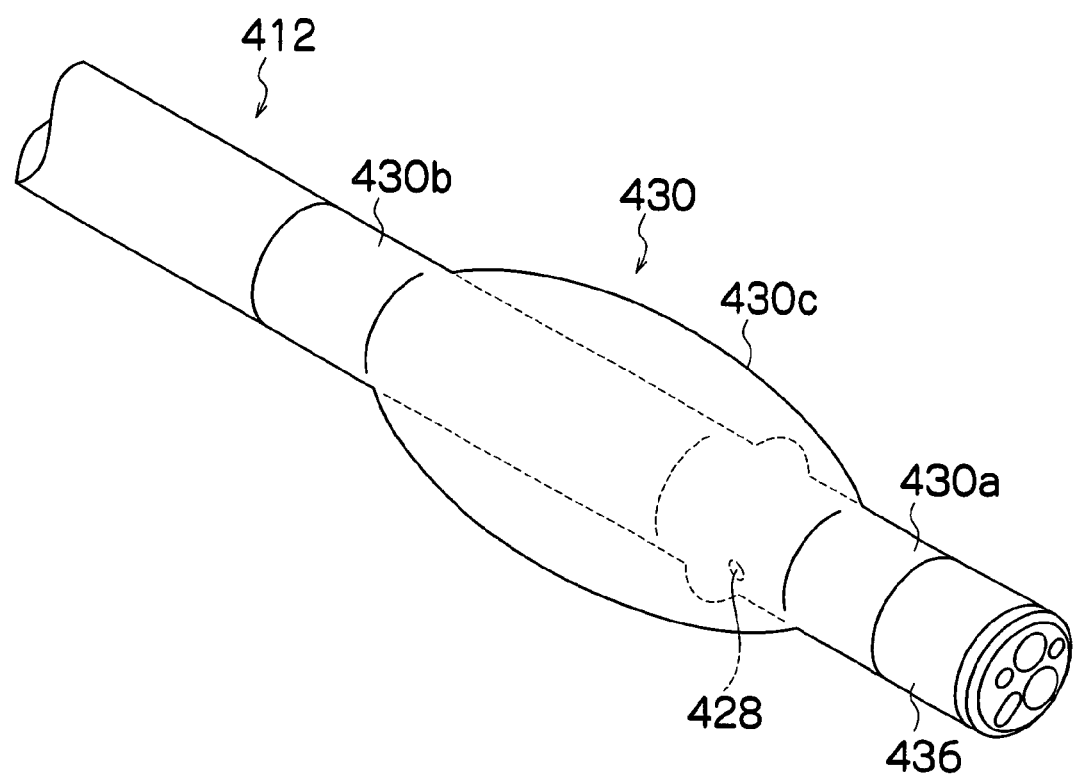
FIG. 19 is a perspective view showing a tip portion of an insert portion equipped with a first balloon.

As shown in FIG. 17, the first balloon 430 made of an elastic body such as rubber is detachably attached to the rigid tip portion 436 of the insert portion 412. As shown in FIG. 19, the first balloon 430 has an inflatable portion 430c in the center and mounting portions 430a and 430b on both ends. It is attached to the rigid tip portion 436 in such a way that the air supply/suction port 428 is located on the inner side of the inflatable portion 430c. The mounting portions 430a and 430b have smaller diameters than the rigid tip portion 436 and the flexible portion 434. They are brought into intimate contact with the rigid tip portion 436 by their own elastic force and then fitted over the outer surface of the rigid tip portion 436 securely with an annular band member (not shown).

Of the first balloon 430 attached to the rigid tip portion 436, the inflatable portion 430c is inflated into an approximately spherical shape by air supplied through the air supply/suction port 428 shown in FIG. 18. When air is sucked through the air supply/suction port 428, the inflatable portion 430c is deflated and brought into intimate contact with the outer surface of the rigid tip portion 436.

Figure 20:
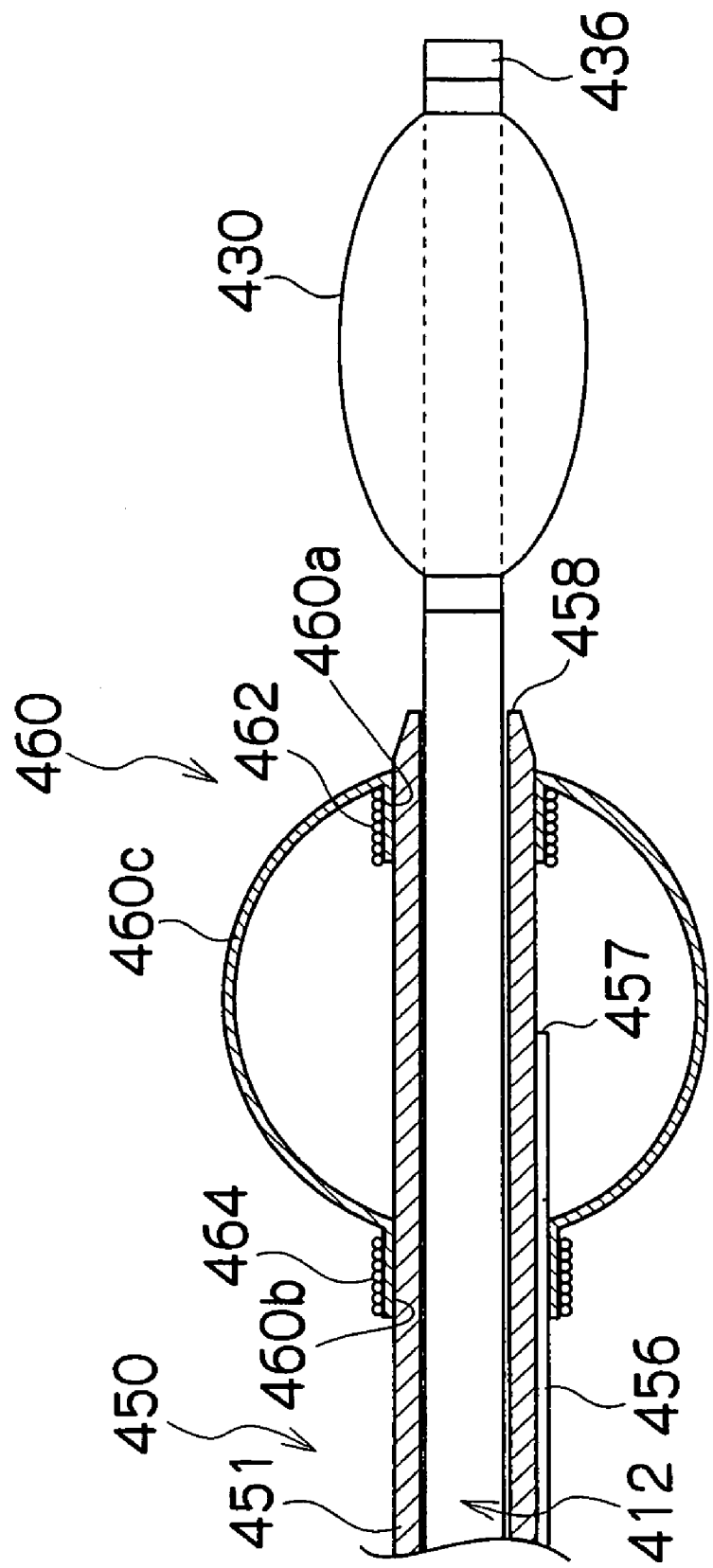
FIG. 20 is a sectional side view of an overtube with an insert portion passed through it.

The overtube 450 shown in FIG. 17 has a tube body 451 and a grip portion 452. As shown in FIG. 20, the tube body 451 is tubular in shape and has an inside diameter slightly larger than the outside diameter of the insert portion 412. Also, the tube body 451 is a molding of flexible urethane resin. Its inner and outer surfaces are covered with a lubricious coating. The grip portion 452 is fitted watertight into the tube body 451 to detachably connect the grip portion 452 to the tube body 451. Incidentally, the insert portion 412 is inserted into the tube body 451 through a base end opening 452A of the grip portion 452.

As shown in FIG. 17, a balloon air feed port 454 is provided at the base end of the tube body 451. The balloon air feed port 454 is connected with an air supply tube 456 approximately 1 mm in inside diameter. Being bonded to the outer surface of the tube body 451, the air supply tube 456 extends to the tip portion of the tube body 451 as shown in FIG. 20.

A tip portion 458 of the tube body 451 is tapered to prevent intestinal walls from being caught in or the like. A second balloon 460 made of an elastic body such as rubber is attached to the base end of the tip portion 458 of the tube body 451 in such a way as to be penetrated by the tube body 451. It has an inflatable portion 460c in the center and mounting portions 460a and 60b on both ends. The mounting portion 460a on the tip side is folded back into the inflatable portion 460c and fastened to the tube body 451, being wound by a radiopaque thread 462. The mounting portion 460b on the base end side is placed outside the second balloon 460 and fastened to the tube body 451, being wound by a thread 464.

The inflatable portion 460c has an approximately spherical shape in normal state (when neither inflated nor deflated) and is larger than the first balloon 430 in normal state (when neither inflated nor deflated). Thus, when air is fed to the first balloon 430 and second balloon 460 at the same pressure, the inflatable portion 460c of the second balloon 460 becomes larger in outside diameter than the inflatable portion 430c of the first balloon 430. For example, when the outside diameter of the first balloon 430 is 25 mm, the outside diameter of the second balloon 460 is 50 mm.

The air supply tube 456 opens into the inflatable portion 460c by forming an air supply/suction port 457. Thus, when air is fed through the balloon air feed port 454, it blows out of the air supply/suction port 457 to inflate the inflatable portion 460c. On the other hand, when air is sucked out of the balloon air feed port 454, it is sucked through the air supply/suction port 457, deflating the second balloon 460.

Incidentally, a strain gauge (pull-out force measuring device: e.g., Wheatstone bridge circuit) 480 is installed at a predetermined location on the insert portion 412 as shown in FIG. 17 to measure the pull-out force of the insert portion 412. Similarly, a strain gauge (pull-out force measuring device: e.g., Wheatstone bridge circuit) 482 is installed at a predetermined location on the tube body 451 of the overtube 450 to measure the pull-out force of the tube body 451. The strain gauges 480 and 482 output electrical signals which represent minute strain in the insert portion 412 and tube body 451.

The strain gauge 480 is connected to one end of a signal line 484, which is laid from the insert portion 412 to the hand controller 414 and extends to the outside from the hand controller 414. The other end of the signal line 484 is connected to a connector 486 of the control apparatus 500. Thus, the electrical signals which come out of the strain gauge 480 and represent electrical resistance are outputted to the control apparatus 500 via the signal line 484.

On the other hand, the strain gauge 482 is connected to one end of a signal line 488, which is laid from the tube body 451 to the grip portion 452 and extends to the outside from the grip portion 452. Thus, the electrical signals which come out of the strain gauge 482 and represent electrical resistance are outputted to the control apparatus 500 via the signal line 488.

The control apparatus 500 supplies and sucks a fluid such as air to/from the first balloon 430 as well as the second balloon 460. Also, it displays electrical resistance corresponding to the pull-out force of the insert portion 412 and pull-out force of the tube body 451 on an LCD display 492 based on the electrical signals outputted from the strain gauges 480 and 482.

The control apparatus 500 includes an apparatus body 502 equipped with a pump, sequencer, etc. (not shown) and a remote control hand switch 504.

A power switch SW1, a stop switch SW2, a pressure gauge 506 for the first balloon 430, and a pressure gauge 508 for the second balloon 460 are installed on a front panel of the apparatus body 502. Also, a tube 510 for use to supply and suck air to/from the first balloon 430 and a tube 520 for use to supply and suck air to/from the second balloon 460 are installed on the front panel of the apparatus body 502. The tubes 510 and 520 have liquid reservoir tanks 530 and 540, respectively, to collect liquid flowing backward from the first balloon 430 and second balloon 460 in case the first balloon 430 and second balloon 460 burst, respectively.

Figure 21:
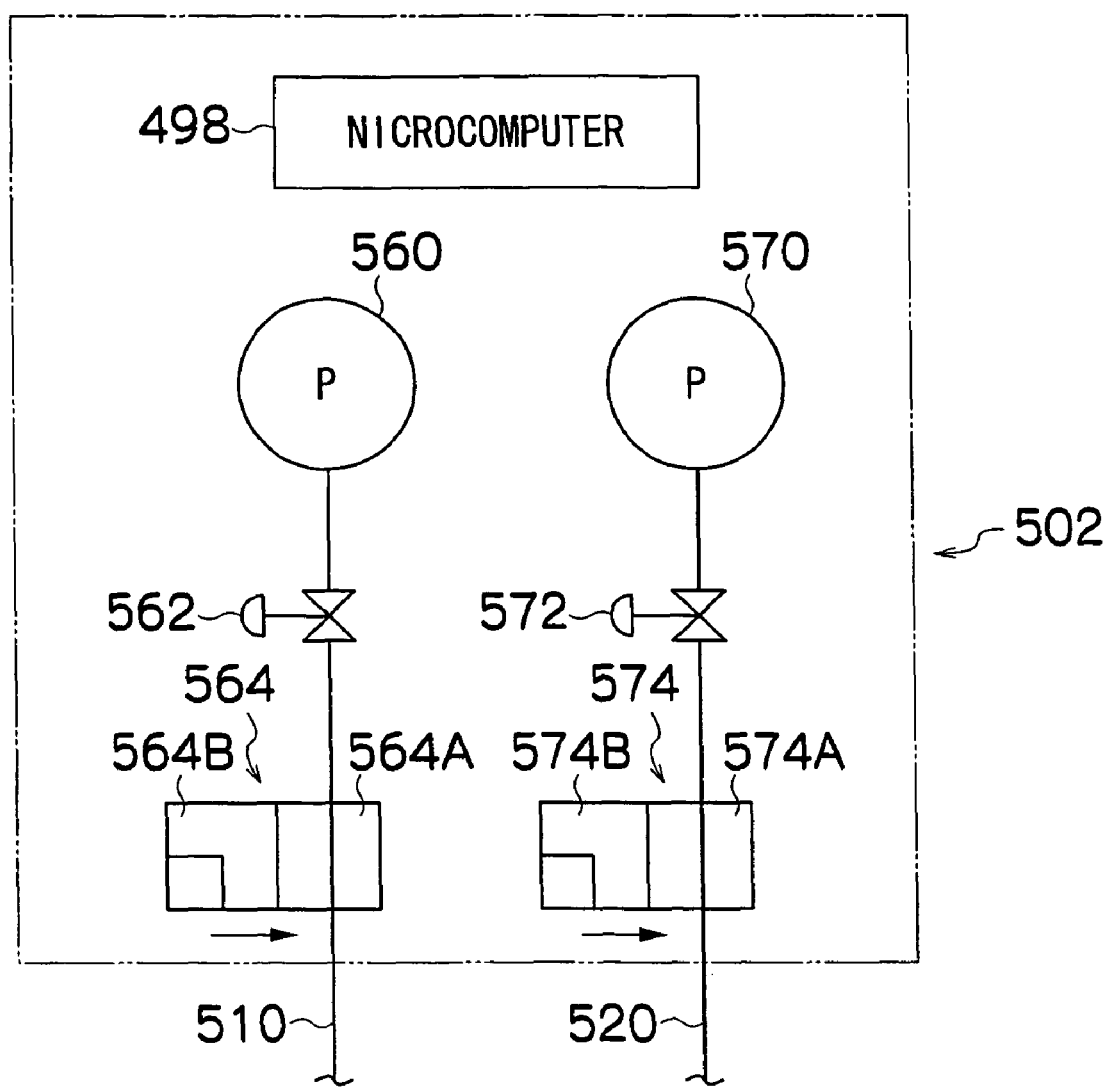
FIG. 21 is a block diagram showing configuration of a balloon pressure regulating device which reduces the internal pressure of a balloon.

Furthermore, the LCD display 492, a resistance setting dial 494, and a warning lamp 496 are installed on the front panel of the apparatus body 502. The resistance setting dial 494 is used to set a threshold of the electrical resistance specified on a microcomputer 498 shown in FIG. 21. That is, it sets thresholds of the pull-out forces (tensile forces) acting on the insert portion 412 and the overtube 450. If a signal which represents a value exceeding the set electrical resistance (pull-out force) is outputted from the strain gauge 480 or 482, the microcomputer 498 turns on the warning lamp 496.

Also, the microcomputer 498 controls a pump 560 and pressurizing/pressure-reducing valve 562 used to feed air to the first balloon 430 based on command signals from the hand switch 504. It switches a change-over valve (balloon pressure regulating device) 564 based on the electrical signal outputted from the strain gauge 480. The change-over valve 564 has a supply gate 564A and leak gate 564B. If a electrical signal outputted from the strain gauge 480 exceeds the set threshold, the change-over valve 564 is switched from the supply gate 564A to the leak gate 564B. Consequently, the air in the first balloon 430 is released to the atmosphere through the tube 510 and the leak gate 564B, decreasing the internal pressure of the first balloon 430.

Furthermore, the microcomputer 498 controls a pump 570 and a pressurizing/pressure-reducing valve 572 used to feed air to the second balloon 460 based on command signals from the hand switch 504. It switches a change-over valve (balloon pressure regulating device) 574 based on the electrical signal outputted from the strain gauge 482. The change-over valve 574 has a supply gate 574A and leak gate 574B. If a electrical signal outputted from the strain gauge 482 exceeds the set threshold, the change-over valve 574 is switched from the supply gate 574A to the leak gate 574B. Consequently, the air in the second balloon 460 is released to the atmosphere through the tube 520 and the leak gate 574B, decreasing the internal pressure of the second balloon 460.

The hand switch 504 shown in FIG. 17 contains a stop switch SW3 similar to the stop switch SW2 of the apparatus body 502, an ON/OFF switch SW4 for pressurization/depressurization of the first balloon 430, a pause switch SW5 for use to maintain the pressure of the first balloon 430, an ON/OFF switch SW6 for pressurization/depressurization of the second balloon 460, and a pause switch SW7 for use to maintain the pressure of the second balloon 460. The hand switch 504 is electrically connected to the microcomputer 498 on the apparatus body 502 via a cable 550.

Being configured as described above, the control apparatus 500 inflates the first balloon 430 and second balloon 460 by supplying air to them and keeps the first balloon 430 and second balloon 460 inflated by maintaining the air pressure at a fixed value. Also, it deflates the first balloon 430 and second balloon 460 by sucking air from them and keeps the first balloon 430 and second balloon 460 deflated by maintaining the air pressure at a fixed value.

Next, an operation method of the endoscope apparatus will be described with reference to FIGS. 22A to 22H.

First, as shown in FIG. 22A, the insert portion 412 is inserted in an intestinal tract (e.g., pars descendens duodeni) 470 with the overtube 450 put over the insert portion 412. At this time, the first balloon 430 and second balloon 460 are kept deflated.

Next, as shown in FIG. 22B, with the tip 458 of the overtube 450 inserted to a bend of the intestinal tract 470, the second balloon 460 is inflated by air supplied to it. Consequently, the second balloon 460 is restrained by the intestinal tract 470 and the tip 458 of the overtube 450 is fixed to the intestinal tract 470.

Next, as shown in FIG. 22C, only the insert portion 412 of the endoscope 410 is inserted into the depth of the intestinal tract 470. Then, as shown in FIG. 22D, the first balloon 430 is inflated by air supplied to it. Consequently, the first balloon 430 is fixed to the intestinal tract 470. Since the first balloon 430 is smaller than the second balloon 460 when inflated, there is less strain on the intestinal tract 470. This prevents damage to the intestinal tract 470.

Next, after the second balloon 460 is deflated with air sucked from it, the overtube 450 is pushed in and inserted together with the insert portion 412 as shown in FIG. 22E. When the tip 458 of the overtube 450 is inserted to near the first balloon 430, the second balloon 460 is inflated with air supplied to it as shown in FIG. 22F. Consequently, the second balloon 460 is fixed to the intestinal tract 470. That is, the intestinal tract 470 is held by the second balloon 460.

Then, as shown in FIG. 22G, the overtube 450 is pulled in. This causes the intestinal tract 470 to contract in a approximately straightened state, eliminating excess bending and flexion of the overtube 450.

Next, as shown in FIG. 22H, the first balloon 430 is deflated with air sucked from it. Then, the rigid tip portion 436 of the insert portion 412 is inserted as deeply as possible into the intestinal tract 470. That is, the insertion operation shown in FIG. 22C is performed again. This allows the rigid tip portion 436 of the insert portion 412 to be inserted into the depth of the intestinal tract 470. To insert the insert portion 412 further, the fixing operation shown in FIG. 22D, the pushing operation shown in FIG. 22E, the holding operation shown in FIG. 22F, the pull-in operation shown in FIG. 22G, and the insertion operation shown in FIG. 22H can be repeated in this order. This allows the insert portion 412 to be inserted more deeply into the intestinal tract 470.

Incidentally, during the pull-in operation shown in FIG. 22G, since the first balloon 430 and second balloon 460 are inflated and placed in intimate contact with the intestinal tract 470, the physician encounters pull-out resistance via the overtube 450 and insert portion 412. The pull-out resistance corresponds to the electrical resistance value which is based on the electrical signal outputted from the strain gauge 480 installed on the insert portion 412 and the electrical resistance value which is based on the electrical signal outputted from the strain gauge 482 installed on the tube body 451. These electrical resistance values are displayed on the LCD display 492 of the balloon control apparatus 100. This allows the physician to quantitatively grasp the pull-out force of the insert portion 412 and pull-out force of the overtube 450 separately.

The microcomputer 498 of the control apparatus 500 contains preset values of electrical resistance corresponding to pull-out forces determined by giving a predetermined margin of safety to pull-out forces which are likely to adversely affect the intestinal tract 470. The microcomputer 498 calculates electrical resistance values based on electrical signals from the strain gauges 480 and 482, and turns on the warning lamp 496 if any calculated electrical resistance value exceeds the preset electrical resistance value. This allows the physician to know that the pull-out force exceeds its preset value and stop the pull-in operation temporarily. If only the electrical resistance value from the strain gauge 480 exceeds its preset value, the change-over valve 564 is switched from the supply gate 564A to the leak gate 564B, reducing the internal pressure of the first balloon 430. If only the electrical resistance value from the strain gauge 482 exceeds its preset value, the change-over valve 574 is switched from the supply gate 574A to the leak gate 574B, reducing the internal pressure of the second balloon 460. Consequently the electrical resistance value is decreased sharply, and thus the intestinal tract 470 is not affected adversely even if the physician continues the pull-in operation.

Incidentally, the switching of the change-over valves 564 and 574 are not essential. The physician who sees from the glow of the warning lamp 496 that the pull-out force exceeds its preset value may reduce the frictional resistance by turning the insert portion 412 or overtube 450 in the intestinal tract 470 before resuming the pull-in operation.

Also, although the overtube 450 with the balloon 460 at the tip has been described in this embodiment, this is not restrictive. The pull-out force measuring device according to this embodiment may be installed on a sliding tube (an applicator without a balloon) used for a colonoscope and the pull-out force of the sliding tube may be determined quantitatively.

Furthermore, although the strain gauge 482 has been cited as an example of the pull-out force measuring device in this embodiment, this is not restrictive. It is possible to construct the overtube 450 or insert portion 412 from translucent rubber, transmit light through a portion which becomes thin when pulled, and measure the pull-out force quantitatively based on light transmittance. Alternatively, it is possible to connect a spring-based measuring device such as a spring scale to the overtube 450 or insert portion 412, pull the overtube 450 or insert portion 412 using the measuring device, and thereby measure the pull-out force.

What is claimed is:

1. An endoscope applicator configured to enable an endoscope insert portion of an endoscope to be inserted through a base end portion of the endoscope applicator and configured to enable lubricant to be provided through a lubricant inlet formed at the base end portion of the endoscope applicator, said applicator comprising:
    a tubular body having a cross-section;
    an elongated lubricant supply conduit eccentric in cross-section relative to the cross-section of the tubular body and extending along an outer surface of the tubular body, the supply conduit in communication with the lubricant inlet; and
    a plurality of openings formed on an inner surface of the tubular body in fluid communication with corresponding openings in the lubricant supply conduit provided along an axial direction from a base end portion to an opposing distal end portion of the tubular body,
    wherein the plurality of openings allows the lubricant provided through the lubricant inlet to be supplied to a clearance between an inner surface of the tubular body and an outer surface of the endoscope insert portion inserted in the tubular body.

2. The endoscope applicator according to claim 1,
    wherein the lubricant supply conduit is laid along an axial direction of the tubular body and extends from the base end portion to a tip end portion of the tubular body,
    the plurality of openings being formed at predetermined intervals from the base end portion to the tip end portion of the tubular body,
    the lubricant poured through the lubricant inlet to the lubricant supply conduit being supplied from the openings to the clearance between the inner surface of the tubular body and the outer surface of the endoscope insertion portion.

3. The endoscope applicator according to claim 2, wherein opening areas of the plurality of openings increase from the base end portion to the tip end portion of the tubular body.

4. The endoscope applicator according to claim 3, wherein a plurality of lubricant supply conduits are provided.

5. The endoscope applicator according to claim 3, wherein the lubricant supply conduit extends spirally on the outer surface of the tubular body.

6. The endoscope applicator according to claim 1, wherein the lubricant supply conduit comprises a gutter member formed on the outer surface of the tubular body, the gutter member having a U-shaped cross-section with an open end.

7. The endoscope applicator according to claim 6, wherein the lubricant supply conduit further comprises a sheet extending along a longitudinal length of the gutter member and across the open end of the U-shaped cross-section to form a supply path for the lubricant in an interior of the gutter member.

8. The endoscope applicator according to claim 1, wherein the lubricant supply conduit is at least partially buried inside the outer surface of the tubular body.

9. An endoscope applicator which is configured to receive an endoscope insert portion of an endoscope to be inserted through a base end portion of the endoscope applicator and enables lubricant to enter through a lubricant inlet formed at the base end portion, said applicator comprising:
    a hollow elongate tube having a cross-section and a tapered distal end opposing said base end;
    a plurality of openings formed in said elongate tube from said base end to said distal end at predetermined intervals;
    a lubricant supply conduit on an outer surface of said elongate tube, said lubricant supply conduit being eccentric in cross-section relative to the cross-section of said elongate tube and in fluid communication with said plurality of openings (75) to form a lubricant supply path from the base end portion to a tip end portion of the elongate tube in an axial direction of the elongate tube, the lubricant supply conduit configured to supply the lubricant from the lubricant inlet via the lubricant supply conduit and the plurality of openings (75) to a clearance between an inner surface of the elongate tube and an outer surface of the endoscope insert portion inserted into the elongate tube.

10. The endoscope applicator according to claim 9, wherein opening areas of the plurality of openings increase from said base end to said distal end.

11. The endoscope applicator according to claim 9, wherein a plurality of lubricant supply conduits are provided.

12. The endoscope applicator according to claim 9, wherein the lubricant supply conduit is provided spirally on an outer surface of the applicator.

13. The endoscope applicator according to claim 9, wherein the lubricant supply conduit comprises a gutter member formed on the outer surface of the elongate tube, the gutter member having a U-shaped cross-section with an open end.

14. The endoscope applicator according to claim 13, wherein the lubricant supply conduit further comprises a sheet extending along a longitudinal length of the gutter member and across the open end of the U-shaped cross-section to form a supply path for the lubricant in an interior of the gutter member.

15. The endoscope applicator according to claim 9, wherein the lubricant supply conduit is at least partially buried inside the outer surface of the elongate tube.

* * * * *